United States Patent [19]
Roberts et al.

[11] Patent Number: 5,417,214
[45] Date of Patent: May 23, 1995

[54] QUANTITATIVE BLOOD FLOW MEASUREMENT USING STEADY-STATE TRANSPORT-INDUCED ADIABATIC FAST PASSAGE

[75] Inventors: David A. Roberts, Drexel Hill; John S. Leigh, Jr., Philadelphia, both of Pa.

[73] Assignee: Trustees of the University of Pennsylvania, Philadelphia, Pa.

[21] Appl. No.: 215,091

[22] Filed: Mar. 18, 1994

Related U.S. Application Data

[62] Division of Ser. No. 927,925, Aug. 7, 1992, Pat. No. 5,320,099.

[51] Int. Cl.$^6$ .............................................. A61B 5/055
[52] U.S. Cl. .................................. 128/653.3; 324/306
[58] Field of Search ........................ 128/653.2, 653.3; 324/306, 309

[56] References Cited

U.S. PATENT DOCUMENTS 4,695,798  9/1987  Brandes .............................. 324/307

OTHER PUBLICATIONS

Dixon et al., "Protection Angiograms of Blood Labelled by Adiabatic Fast Passage", Magnetic Resonance in Medicine, vol. 3, pp. 454–462 (1986).
Dumoulin et al., "Magnetic Resonance Angiography", Radiology, vol. 161, pp. 717–720 (Dec. 1986).
Edelman et al., "Quantification of Blood Flow with Dynamic MR Imaging and Presaturations Bolus Tracking", Radiology, vol. 171, pp. 551–556 (1989).
Firmin rt al., "Echo Planar High Life and Resolution Flow Velocity Mapping", Magnetic Resonance in Medicine, vol. 12, pp. 316–327 (1989).
Grad et al., "Nuclear Magnetic Cross-Relaxation Spectroscopy", Journal of Magnetic Resonance, vol. 90, pp. 1–8 (1990).
Gullberg et al., "MR Vascular Imaging with a Fast Gradient Refocusing Pulse Sequence and Reformatted Wolff et al., "Magnetization Transfer Contrast (MTC) and Tissue Water Proton Relaxation in Vivo", Magnetic Resonance in Medicine, vol. 10, pp. 135–144 (1989).

(List continued on next page.)

*Primary Examiner*—Ruth S. Smith
*Attorney, Agent, or Firm*—Woodcock Washburn Kurtz Mackiewicz & Norris

[57] ABSTRACT

A subtractive time of flight technique for MR angiography and quantitative blood flow measurement. Proton spins of water in the arterial supply to a tissue or organ are inverted in a steady-state fashion by applying constant amplitude off-resonance radio frequency pulses in the presence of a constant linear magnetic field gradient to effect adiabatic fast passage transport-induced inversion of spins which move in the direction of the gradient. An angiogram is formed by subtracting an image acquired with the arterial inversion pulse from a control image acquired with no arterial inversion. By inverting the spins in a steady-state manner, no cardiac gating is necessary for imaging organs. However, cardiac gating is desirable when imaging the heart so that spins of blood passing through the coronary arteries can be inverted during systole, when most of the blood is in the left ventricle, and imaged at end diastole, when most of the blood is in the coronary arteries. A coronary angiogram is then formed by subtracting images acquired with and without the inversion pulse. Also, by applying several inverting and imaging pulses during a cardiac cycle in accordance with the technique of the invention, a characteristic banding pattern may be formed in the fluid whereby each band corresponds to a population of spins that experienced inversion due to a single RF pulse. Since the width of the inversion band is proportional to the duration of the RF pulse and the velocity of the spin, measurement of the thickness of the inverted and uninverted bands allows for calculation of flow velocity. By gating such a pulse sequence to the cardiac cycle, time resolved in vivo velocity measurements may be made.

5 Claims, 20 Drawing Sheets

OTHER PUBLICATIONS

Images from Transaxial Sections", Radiology, vol. 165, pp. 241–246 (1987).

Le Bihan et al., "MR Imaging of Intravoxel Incoherent Motions: Application to Diffusion and Perfusion in Neurologica Disorders" Radiology, vol. 161, pp. 401–407 (1986).

Lee et al. "Spatially Resolved Low Velocity Measurements and Projection Angiography by Adiabatic Passage", Magnetic Resonance Imaging, vol. 9, pp. 115–127 (1991).

Nayler et al., "Blood Flow Imaging by Cine Magnetic Resonance", The Journal of Computer Assisted Tomography, vol. 10, pp. 715–722 (1986).

Nishimura et al., "Considerations of Magnetic Angiography by Selective Inversion Recovery", Magnetic Resonance in Medicine, vol. 7, pp. 472–484 (1988).

Nishimura et al., "Magnetic Resonance Angiography by Selective Inversion Recovery using a Compact Gradient Echo Sequence", Magnetic Resonance in Medicine, vol. 8, pp. 96–103 (1988).

Nishimura et al., "MR Angiography by Selective Inversion Recovery", Magnetic Resonance in Medicine, vol. 4, pp. 193–202 (1987).

Saloner et al., "Flow Velocity Quantitation using Inversion Tagging", Magnetic Resonance in Medicine, vol. 16, pp. 269–279 (1990).

Sardashti et al., "Spin-Labelling Angiography of the Carotids by Presaturation & Simplified Adiabatic Inversion", Magnetic Resonance in Medicine, vol. 15, pp. 192–200 (1990).

Wang et al., "Fast Angiography using Selective Inversion Recovery", Magnetic Resonance in Medicine, vol. 23, pp. 109–121 (1992).

Wedeen et al., "Projective MRI Angiography and Quantitative Flow-Volume Densitometry", Magnetic Resonance in Medicine, vol. 3, pp. 226–241, (1986).

Williams et al., "Magnetic Resonance Imaging of Perfusion using Spring Inversion of Arterial Water", Proceedings of the National Academy of Science, vol. 89, pp. 212–216 (1992).

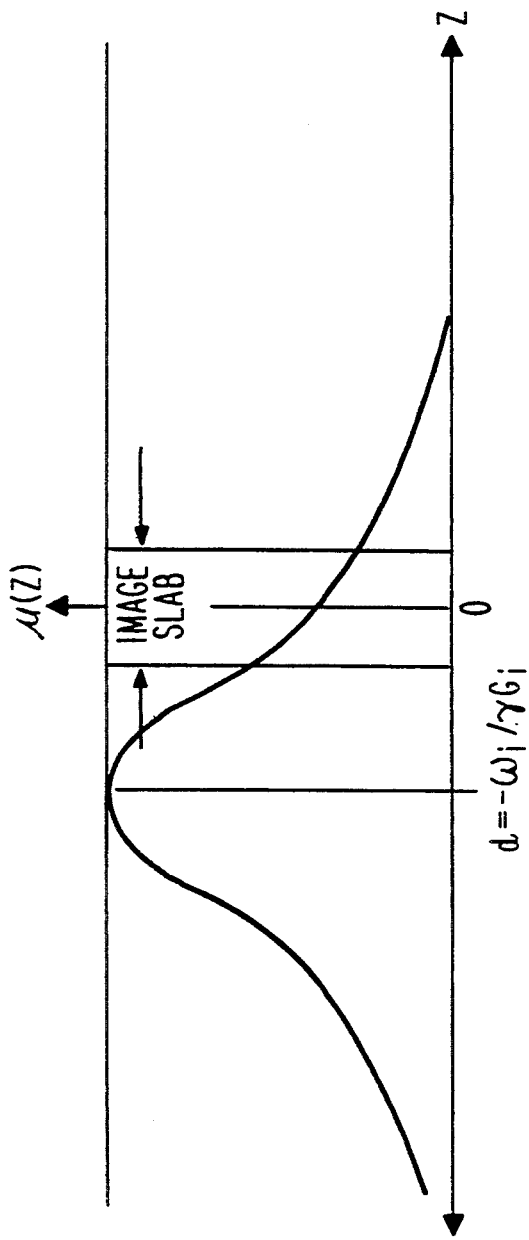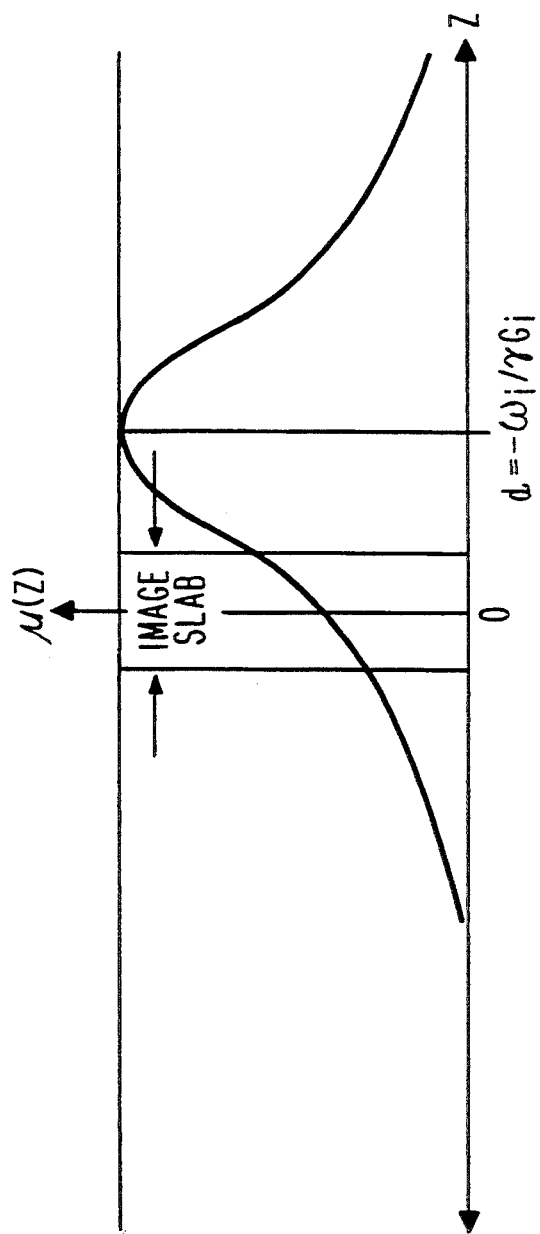
Fig. 3(a)
Fig. 3(b)

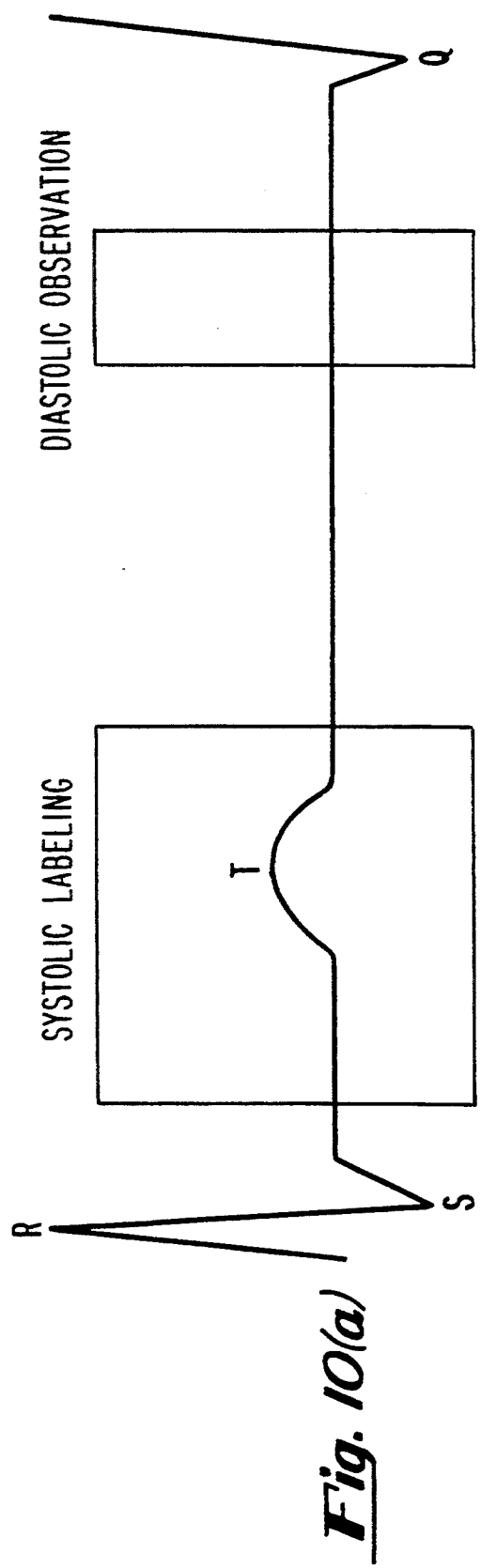
Fig. 10(a)
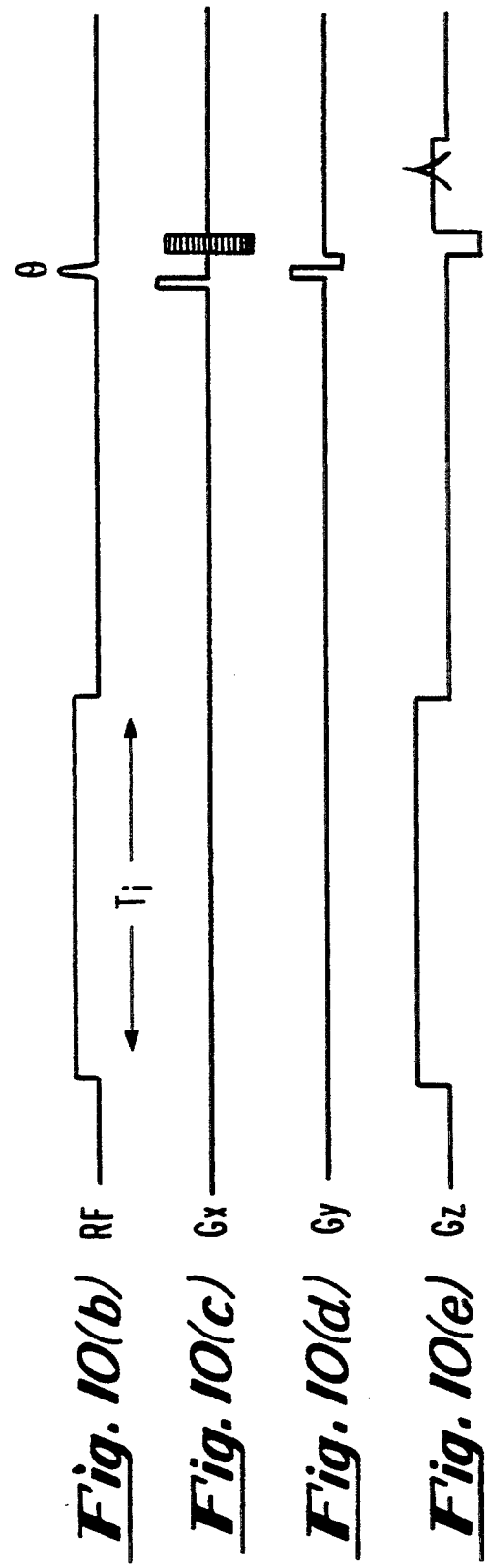
Fig. 10(b) RF
Fig. 10(c) Gx
Fig. 10(d) Gy
Fig. 10(e) Gz

QUANTITATIVE BLOOD FLOW MEASUREMENT USING STEADY-STATE TRANSPORT-INDUCED ADIABATIC FAST PASSAGE

This is a division of application Ser. No. 07/927,925, filed Aug. 7, 1992, U.S. Pat. No. 5,320,099.

BACKGROUND OF THE INVENTION

1. Field of the Invention

The present invention relates to a technique for MR angiography and quantitative blood flow measurement, and more particularly, to techniques for MR angiography using steady-state transport-induced adiabatic fast passage and for quantitative MR flow measurement using pulsed adiabatic inversion.

2. Description of the Prior Art

The measurement of tissue perfusion, i.e., the flow of fluid in tissue, and of quantitative blood flow in arteries is important for the functional assessment of organs in vivo. Although the terms perfusion and flow are sometimes used interchangeably, perfusion as used herein is a quantifiable measurement of capillary blood flow which is generally measured indirectly in humans, while flow refers to the quantitative volume of blood passing through an artery in a given period of time. Angiograms, on the other hand, provide a qualitative view of arteries, tissues and the like which is useful for diagnostic purposes. Numerous techniques have been developed in the prior art for providing angiograms as well as measurements of perfusion and blood flow using magnetic resonance imaging.

For example, in U.S. patent application Ser. No. 746,771, filed Aug. 16, 1991, now U.S. Pat. No. 5,402,785 and in an article entitled "Magnetic Resonance Imaging of Perfusion Using Spin Inversion of Arterial Water", *Proc Natl Acad Sci.*, Vol. 89, pp 212-216 (1992), one of the present inventors disclosed a method for measuring perfusion by labeling proton spins of inflowing water in the arterial blood using magnetic resonance. Continuous saturation or continuous inversion using an adiabatic excitation was then performed proximal to the tissue or organ of interest. In particular, perfusion was measured by labeling atoms in the blood at a base point, generating a steady state in the tissue or organ by continuing to label atoms until the effect caused by labeled atoms perfusing into the tissue or organ reaches a steady state, generating imaging information for the tissue or organ, and processing the imaging information to determine perfusion. In a particular embodiment of that invention, by continuously applying a radio-frequency (RF) field, spins associated with the atoms were inverted continuously by adiabatic fast passage. This technique was disclosed for determining perfusion in the brain as well as other tissues or organs having well defined arterial supplies such as the kidney, the liver and the heart.

Spin inversion was preferred for perturbing the magnetization of the arterial water in accordance with the technique of the above-identified application because it maximized the observed effect. In order to invert the arterial spins continuously as described therein, an RF signal was applied in the presence of a magnetic field gradient in the direction of the flow so that the movement of the spins through the magnetic field gradient leads to a change in the magnetic field through resonance. As described therein, this approach has lead to greatly improved images of tissue perfusion in the brain and other organs.

However, since the contribution from the arterial intravascular volume must be eliminated in order to get accurate measurements of tissue perfusion, the technique described in the aforementioned patent application is not suitable for quantitatively measuring blood flow or for acquiring an MR angiogram. On the contrary, the technique described in the aforementioned patent application requires symmetrical spoiler gradient pulses to be used in the imaging sequence around the 180° pulse to eliminate arterial intravascular signals in both the proximal and the control saturation images. This minimizes the affects on intravascular spins of proximal saturation, which otherwise causes the difference image to include a contribution from the arterial intravascular volume in addition to a contribution caused by the exchange of labeled vascular water with tissue water during the perfusion measurement. In other words, spoiler gradients have been used when obtaining images of tissue perfusion in order to eliminate signal contribution from the moving spins. For this reason, while providing an excellent technique for measuring perfusion, the technique described in the aforementioned patent application cannot be used for MR angiography and quantitative blood flow measurement.

Recently, several subtractive time-of-flight (TOF) magnetic resonance angiography (MRA) techniques have been described in the art. For example, such techniques are described by Dixon et al. in an article entitled "Projection Angiograms of Blood Labeled by Adiabatic Fast Passage", *Magnetic Resonance in Medicine*, Vol. 3, pp. 454-462 (1986); by Nishimura et al. in articles entitled "MR Angiography By Selective Inversion Recovery", *Magnetic Resonance in Medicine*, Vol. 4, pp. 193-202 (1987), "Considerations of Magnetic Resonance Angiography By Selective Inversion Recovery", *Magnetic Resonance in Medicine*, Vol. 7, pp.472-484 (1988), and "Magnetic Resonance Angiography By Selective Inversion Recovery Using A Compact Gradient Echo Sequence", *Magnetic Resonance in Medicine*, Vol. 8, pp 96-103 (1988); by Sardashti et al. in an article entitled "Spin-Labeling Angiography of the Carotids By Presaturation and Simplified Adiabatic Inversion", *Magnetic Resonance in Medicine*, Vol. 15, pp. 192-200 (1990); and by Wang et al. in an article entitled "Fast Angiography using Selective Inversion Recovery", *Magnetic Resonance in Medicine*, Vol. 23, pp. 109-121 (1992). The techniques described in those articles complement conventional phase-contrast techniques such as those described by Dumoulin et al. in an article entitled "Magnetic Resonance Angiography", *Radiology*, Vol. 161, pp. 717-720 (1986); by Wedeen et al. in an article entitled "Projective MRI Angiography and Quantitative Flow-Volume Densitometry", *Magnetic Resonance in Medicine*, Vol. 3, pp. 226-241 (1986); and by Nayler et al. in an article entitled "Blood Flow Imaging by Cine Magnetic Resonance", *Journal of Computer Assisted Tomography*, Vol. 10, pp. 715-722 (1986), and conventional time-of-flight MRA techniques such as those described by Gullberg et al. in an article entitled "MR Vascular Imaging With a Fast Gradient Refocusing Pulse Sequence and Reformatted Images From Transaxial Sections", *Radiology*, Vol 165, pp. 241-246 (1987).

Dixon et al. describe an approach to MR angiography in which a constant RF pulse is transmitted through a separate surface coil in the presence of a constant magnetic gradient so that moving spins undergo adiabatic fast passage inversion. By turning the inversion RF on and off during alternate gated acquisitions, Dixon et al. generated images with and without labeled blood. An angiogram was then formed by simple subtraction for visualizing, for example, the carotid bifurcation.

In accordance with the Dixon et al. technique, all the blood passing the RF surface coil while the RF signal is being applied is labeled and then allowed to flow for a period of time so that it can enter the imaging volume. The longest possible labeling time is used which is consistent with the number of cardiac cycles chosen for TR. It is thus important in using the Dixon et al. technique that the RF signal be turned on and off slowly to prevent saturation of stationary tissue near the RF surface coil. It is also important that little power be used so as to prevent heating of the tissue of the patient in the vicinity of the RF surface coil. Moreover, in accordance with the technique of Dixon et al., since the phase encodings are interleaved and the labeled blood must be given time to propagate into the imaging volume before acquiring the image, only one phase encoding per cardiac cycle is possible. Furthermore, since this process is synchronized to the cardiac cycle by cardiac gating so as to phase encode every cardiac cycle with 90° and 180° pulses, the appropriate propagation time delay must also be selected to allow the labeled column of blood enough time to fill the arteries that are being imaged. Accordingly, Dixon et al. must estimate how far the spins travel in a selected period of time in order to maintain synchronization. An improved approach is desired which does not require synchronization to the cardiac cycle and which allows for fast scan imaging.

Another approach to MRA, referred to as selective inversion recovery (SIR) (as described in the aforementioned articles to Nishimura et al., Sardashti et al. and Wang et al.), uses spatially selective inversion pulses to label a column of arterial blood which then flows into an organ in the imaging region. Selective 180° excitation inverts different regions between measurements to isolate arterial and/or venous blood so that high-resolution carotid artery angiograms and the like may be obtained. A 90° presaturation pulse may also be applied to suppress the background intensity from static tissue in the angiogram, which is formed by subtracting an image acquired with inversion from an image acquired without inversion. As an inversion technique, SIR of the arterial inflow to an organ has been found to offer excellent angiographic contrast and penetration due to the fact that blood is inverted, not just saturated. As a subtractive technique, SIR also provides excellent background suppression, similar to that of phase contrast techniques.

However, there are also some problems associated with SIR techniques which use spatially selective inversion pulses to label blood flow. In general, these techniques must be gated to the cardiac cycle so that complete labeling of the inflowing blood occurs. In addition, the inversion pulses used to label blood flow should have precisely defined passbands in order for complete inversion to occur. This typically involves the use of complicated RF pulse shapes. Another drawback of SIR is the fact that spins in the more distal parts of the labeled column of blood undergo T1-relaxation as they traverse the slab thickness. The spins therefore lose part of the label before entering the imaging volume, leading to a loss of angiographic contrast. An improved angiographic technique is desired which overcomes such problems.

Various time-of-flight (TOF) methods have also been described in the prior art for quantitative NMR flow measurement. For example, Saloner et al. disclose in an article entitled "Flow Velocity Quantitation Using Inversion Tagging", *Magnetic Resonance in Medicine*, Vol. 16, pp. 269–274 (1990) and Edelman et al. disclose in an article entitled "Quantification of Blood Flow With Dynamic MR Imaging and Presaturation Bolus Tracking", *Radiology*, Vol. 171, pp. 551–556 (1989) methods employing spatially localized saturation or inversion RF pulses for labeling moving spins. In these approaches, a column of fluid is subjected to a series of spatially-selective RF pulses in a steady-state imaging experiment. This results in a banding pattern in the fluid from which the velocity may be determined. However, these methods are subject to errors arising from motion of the spins during application of the spatially selective RF pulses. In addition, the accuracy of these methods also depends on the characteristics of the spatially-selective inversion pulses used to tag the fluid. In general, optimized RF pulses must be used in order for accurate velocity measurements to be made. Unfortunately, due to the fact that each group of "tagged" spins experiences multiple RF pulses during transit through the inverted slab, contrast between bands decreases as the flow moves downstream. This effect makes it more difficult to observe the evolution of the banding pattern as the fluid flows distal to the inversion plane.

Lee et al. describe another flow measurement technique in an article entitled "Spatially Resolved Flow Velocity Measurements and Projection Angiography by Adiabatic Passage", *Magnetic Resonance Imaging*, Vol. 9, pp. 115–127 (1991), which provides direct assessment of in-plane and oblique directional flow velocities and visualization of flow velocity profiles as well as flow angiography based on the time-of-flight technique. In particular, Lee et al. generate a band in the liquid which may be used for measuring flow velocity by applying a fast adiabatic passage pulse after a cardiac gated sequence and then applying a spin echo sequence for acquiring the image. A 180° RF pulse is also applied for stationary spin suppression prior to the adiabatic fast passage pulse and a 90° RF pulse is applied prior to phase encoding. Unfortunately, Lee et al. do not sequence fast enough to see plural bands in a single cardiac cycle, and since the 90° and 180° gradient pulses are used, fast scanning techniques cannot be used. Hence, the system of Lee et al. does not provide optimized time resolution of the images taken during the cardiac cycle. An improved MR flow measurement technique is desired which will allow for fast scanning of the slab so as to improve time resolution.

The present invention has been designed to overcome the aforementioned limitations in the prior art by providing a comprehensive system for MR angiography and MR blood flow measurement for different regions of the body. As will be clear from the following description, the present inventors have found that improved MR images of arteries, veins and tissues may be produced using a steady-state adiabatic inversion technique and that blood flow may be measured by adiabatically inverting spins in the direction of the magnetic gradient. The present invention is thus believed to meet long felt needs in the prior art in that it provides for the first time a methodology which allows for MR angiography as well as quantitative blood flow and tissue perfusion measurement of any tissue or organ having a well defined arterial supply.

SUMMARY OF THE INVENTION

The above-mentioned long-felt needs of the prior art have been met in accordance with the present invention by providing a subtractive time-of-flight technique which is related to the pulse inversion approach described by Dixon et al. except that in accordance with the technique of the invention the blood supply to an organ is continuously inverted as it flows into the imaging region. This is accomplished by applying an off-resonance RF pulse in the presence of a constant magnetic field gradient. Since the RF pulse is applied in a steady-state imaging sequence, cardiac gating is not necessary. Also, since a single coil is used for application of the inversion and observation pulses in accordance with the invention, inversion of the arterial supply may occur very close to the imaging volume, thereby minimizing transit time effects. This adiabatic spin inversion angiography technique of the invention has been used to perform intracranial MRA and coronary MRA at 1.5 Tesla, although those skilled in the art will appreciate that the technique of the invention may be applied to other tissues and organs as well.

When imaging the vasculature of an organ in accordance with the techniques of the invention, a single coil can be used to invert blood at an arbitrary location in the imaging volume using the principle of transport-induced adiabatic fast passage inversion. However, due to the complex geometry of the heart, a "localizer" image must first be taken which allows the MR operator to choose an imaging plane in the lateral anterior descending artery or an imaging plane which transects the aortic valve of the heart on its longitudinal axis across the entire curve of the aorta and to establish an inversion plane at a point inferior to the aortic valve so that the resulting angiogram will be meaningful. Then, by applying the inversion pulse in the inversion plane during ejection of blood by the left ventricle (systole), all blood ejected into the coronary arteries may be labeled. The imaging sequence is then applied to the imaging plane in late diastole in order to observe the blood in the coronary arteries. In this manner, the present invention makes possible for the first time coronary angiography as well as coronary blood flow measurement using magnetic resonance.

Also, by using a simple time-of-flight technique for measuring flow velocity using constant amplitude RF pulses in the presence of a gradient to adiabatically invert spins which move in the direction of the gradient, the technique of the invention has been found to further provide a simplified technique for noninvasive quantitative blood flow measurement using magnetic resonance. For example, a preferred embodiment of a method of quantitatively measuring flow in a vessel using magnetic resonance in accordance with the invention comprises the steps of:

(a) applying to the vessel an external substantially uniform magnetic field so as to align predetermined nuclei of a fluid in the vessel with a constant magnetic field gradient of the magnetic field, the predetermined nuclei having a particular resonance frequency;

(b) applying a substantially constant amplitude tagging radio-frequency (RF) pulse having a frequency different from the particular resonance frequency at an inversion plane in the vessel which is transverse to the magnetic field gradient and transverse to a flow direction of the fluid, the tagging RF pulse being applied in the presence of the constant magnetic field gradient so as to invert spins of those predetermined nuclei which have a component of velocity in a direction of the magnetic field gradient as the predetermined nuclei pass through the inversion plane;

(c) applying an observation RF pulse for acquiring an image of a band which results as the inverted spins of the predetermined nuclei flow downstream from the inversion plane in the vessel;

(d) repeating steps (a)-(c) during a predetermined time interval so as to generate a pattern of bands representing inverted spins of nuclei which have flowed downstream from the inversion plane in the vessel during the predetermined time interval; and (e) calculating the flow velocity, v, of the fluid in the vessel from the duration, $T_i$, of a particular tagging RF pulse and the length, $\Delta$, of the corresponding band in accordance with the relationship $\Delta = (v)(T_i)$.

BRIEF DESCRIPTION OF THE DRAWINGS

The above and other objects and advantages of the invention will become more apparent and more readily appreciated from the following detailed description of the presently preferred exemplary embodiments of the invention taken in conjunction with the accompanying drawings, of which:

FIGS. 3(a) and 3(b) together illustrate the effect of magnetization transfer on the technique of the invention where it is assumed that the control image is acquired by changing the sign of an inversion gradient in the slat-selection direction.

FIGS. 10(a), 10(b), 10(c), 10(d) and 10(e) together illustrate a pulse sequence used to form coronary angiograms using transport-induced adiabatic fast passage whereby a constant-amplitude off-resonance RF pulse in the presence of a constant gradient in the frequency-encoding direction proceeds a standard two-dimensional gradient-echo imaging sequence.

FIGS. 12(a), 12(b), 12(c) and 12(d) together illustrate the effect of a constant RF pulse on a spin moving through a gradient at constant velocity, whereby as the spin moves through the gradient, G, it undergoes a frequency sweep.

DETAILED DESCRIPTION OF THE PRESENTLY PREFERRED EXEMPLARY EMBODIMENTS

The MR angiography and MR flow measurement techniques in accordance with the presently preferred exemplary embodiments of the invention will be described below with reference to FIGS. 1–20. The MR angiography technique of the invention using steady-state transport-induced adiabatic fast passage will first be described in connection with Example 1 (intracranial angiography) and FIGS. 1–8. Then, coronary angiography using transport-induced adiabatic fast passage in accordance with the invention will be described in connection with Example 2 (coronary angiography) and FIGS. 9–11. Finally, a technique for quantitative NMR flow measurement using pulsed adiabatic inversion in accordance with the invention will be described with respect to Example 3 for phantom studies (FIGS. 12–16) and studies of the carotid artery (FIGS. 17–20). It will be appreciated by those of ordinary skill in the art that the description given herein with respect to these figures and examples is for exemplary purposes only and is not intended in any way to limit the scope of the invention. All questions regarding the scope of the invention may be resolved by referring to the appended claims.

MR Angiography Using Steady-State Transport-Induced Adiabatic Fast Passage

Theory

Figure 1:
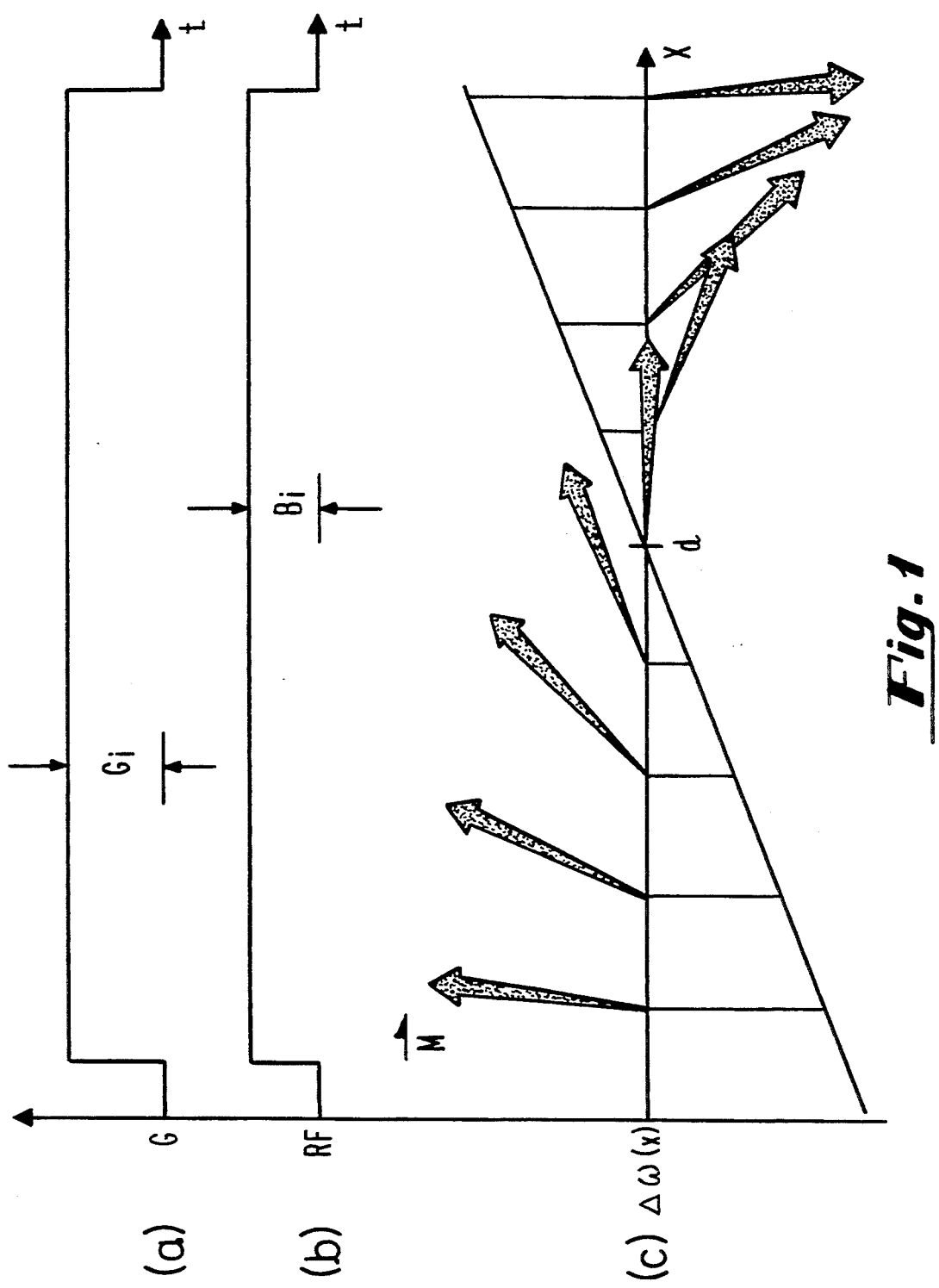
FIGS. 1(a) 1(b) and 1(c) together illustrate the effect of a constant RF pulse on a spin moving through a gradient at constant velocity, whereby as a spin moves through the gradient, $G_i$, it undergoes a frequency sweep as its instantaneous frequency changes linearly with time.

Application of a constant, transverse RF field, $B_i$, in the presence of a magnetic field gradient, $\vec{G}_i$, results in adiabatic inversion of spins which have a component of velocity in the direction of the gradient as illustrated in FIG. 1. In particular, FIG. 1 illustrates the effect of a constant RF pulse on a spin moving through a gradient at constant velocity. As shown, as a spin moves through the gradient, $G_i$ (FIG. 1(a)), it undergoes a frequency sweep as its instantaneous frequency changes linearly with time. As shown, the off-resonance component $\Delta\omega(k)$, where k=x, y or z, of the effective RF field, $B_i$ (FIG. 1(b)), is swept from a large positive value to a large negative value (FIG. 1(c)). As will be shown below, if the rate of change of the frequency is slow enough or if the strength of the RF signal is large enough, the magnetization will follow the effective field and adiabatic inversion will occur.. This general approach has previously been applied to angiography and perfusion imaging by Dixon et al. and Williams et al. in the aforementioned patent application. As described therein, the strength of the gradient, $G_i$, and the velocity, v, of the spin define the effective "sweep rate" for a moving spin in direct analogy to continuous-wave adiabatic fast passage. The present inventors have now discovered that for adiabatic inversion to occur, the velocity should satisfy the following equation:

$$\frac{1}{T_1}, \frac{1}{T_2} << (1/B_i)\, G_i \cdot v < \gamma B_i/2, \qquad \text{Equation 1}$$

where $T_1$ and $T_2$ are the relaxation times of the spin, $\gamma$ is the gyromagnetic ratio, and $B_i$ is the strength of the off-resonance RF signal. Equation 1 illustrates that if a spin moves too slowly, relaxation effects dominate and inversion does not occur, while conversely, if a spin moves too rapidly, incomplete inversion will occur because the sweep becomes non-adiabatic. The efficiency of an inversion pulse may thus be defined as:

$$\alpha = (M_0 - M_z)/2M_0 \qquad \text{Equation 2}$$

where $M_0$ and $M_z$ are the z magnetizations before and after the inversion pulse, respectively. Complete inversion corresponds to $\alpha=1$.

Figure 2:
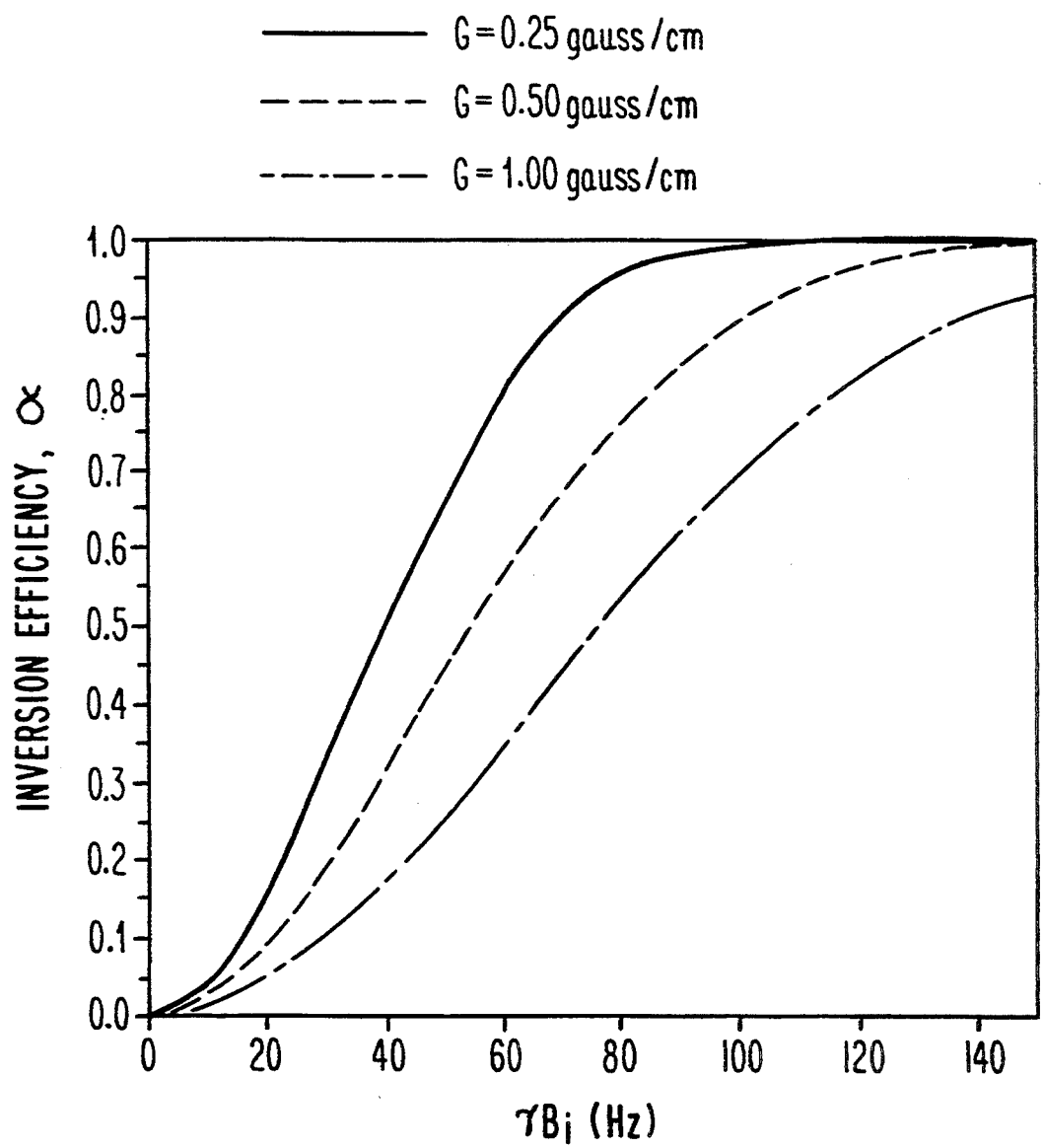
FIG. 2 illustrates the simulated inversion efficiency, $\alpha$, versus the amplitude, $B_i$, of the inversion pulse for three different gradient strengths.

FIG. 2 illustrates the results of computer simulations of spins moving in the presence of such an inversion pulse. The computer simulation was performed using a spinor approximation of the Bloch equation. As illustrated, the simulated inversion efficiency, $\alpha$, is plotted versus the strength, $\gamma B_i$, of the inversion pulse for three different gradient strengths. For the purposes of calculation, the velocity of the spin was assumed to be 20 cm/sec. As expected, FIG. 2 illustrates that the inversion efficiency increases with increasing $B_i$. FIG. 2 also shows that the inversion efficiency may be increased by decreasing the strength of the inversion gradient.

The off-resonance RF pulse described above defines a plane of inversion. Any spin which moves through this plane will experience adiabatic inversion as long as its velocity satisfies the conditions of Equation 1. The distance, d, between the inversion plane and isocenter is given by:

$$d = \omega_i/(\gamma G_i), \qquad \text{Equation 3}$$

where $\omega_i$ is the frequency of the off-resonance pulse relative to the spectrometer frequency. The plane of inversion is perpendicular to the inversion gradient $G_i$.

By preceding a standard imaging sequence with an off-resonance RF pulse in the presence of an inversion gradient in the slice-selection direction, the present inventors have discovered that steady-state inversion of the arterial inflow to an organ may be achieved. Because the fraction of the arterial inflow which is inverted is directly proportional to the duty cycle of the inversion pulse (i.e., the portion of TR including the inversion pulse), the inversion pulse should occupy as much of the interpulse interval as possible. An angiogram can then be formed by subtracting an image acquired with the inversion pulse present from a control image acquired without arterial inversion.

As noted by Wolff et al. in an article entitled "Magnetization Transfer Contrast (MTC) and Tissue Water Proton Relaxation In Vivo", *Magnetic Resonance in Medicine*, Vol. 10, pp. 135–144 (1989), the presence of magnetization transfer in tissues complicates the proper choice of a control image. Indeed, because it is desired to use a single coil in accordance with the invention, the off-resonance pulses used to effect inversion will partially saturate the broad component of the proton signal, leading to magnetization transfer to spins in the image plane. This immediately implies that a control image may not be acquired simply by reducing the amplitude of the inversion pulse to zero since the magnetization transfer effect would be completely unbalanced. Fortunately, as will be described below, approximate control for the magnetization transfer effect may be achieved by other means in accordance with the invention.

For example, if $M_f$ and $M_f^0$ are the equilibrium magnetizations of unbound protons in the presence and absence, respectively, of an off-resonance RF pulse of frequency $\omega_i$ and strength $B_i$ and it is assumed that the inversion pulse is applied in the presence of a gradient, $G_i$, in the slice-selection direction, then the degree of magnetization transfer, $\mu$, to unbound spins due to the off-resonance pulse may be defined as:

$$\mu = (M_f^0 - M_f)/(2 M_f^0). \qquad \text{Equation 4}$$

The dependence of $\mu$ on the frequency offset of the RF pulse, $\Delta = \omega_s - \omega_i$ (where $\omega_s$ is the resonance frequency of the spin in the presence of the gradient) is given by:

$$\mu = \mu(\Delta) = K_1/(K_2 + \Delta^2), \qquad \text{Equation 5}$$

where $K_1$ and $K_2$ are constants which depend on the relaxation characteristics of the two spin populations as described by Grad et al. in an article entitled, "Nuclear Magnetic Cross-Relaxation Spectroscopy", *Journal of Magnetic Resonance*, Vol. 90, p. 1 (1990). These constants depend on the spin distribution and are therefore functions of position, that is, $K_1 = K_1(z)$ and $K_2 = K_2(z)$. In the presence of an inversion gradient, $G_i$, in the z-direction, the frequency offset becomes:

$$\Delta = \gamma G_i(z - d), \qquad \text{Equation 6}$$

where d is given by Equation 3 above. The degree of magnetization transfer in the inversion image, $\mu_i$, as a function of position is then given by:

$$\mu_i(z) = K_1(z)/[K_2(z) + \gamma^2 G_i^2(z - d)^2]. \qquad \text{Equation 7}$$

If a "control" image is acquired with an inversion gradient of opposite sign or, equivalently, with the frequency offset of the inversion pulse reversed, the location of the plane of inversion changes sign to $-d$. In this case, the degree of magnetization transfer in the control image, $\mu_c$, as a function of position is:

$$\mu_c(z) = K_1(z)/[K_2(z) + \gamma^2 G_i^2(z + d)^2]. \qquad \text{Equation 8}$$

Equations 7 and 8 imply that the difference in signal between control and inversion images is zero if and only if $z = 0$, that is, for spins at isocenter. For spins which are not at isocenter in the direction of the inversion gradient (z is not equal to 0), the magnetization transfer effect is not properly controlled and incomplete background suppression will occur.

An example where the magnetization transfer effect is not properly controlled and hence incomplete background suppression will occur is illustrated in FIG. 3. In FIG. 3, it is assumed that the control image is acquired by changing the sign of an inversion gradient in the slab selection direction. Due to dispersion of magnetization transfer in the slab selection direction, the same signal on inversion and control images is obtained only for spins at isocenter, i.e., $z = 0$.

If, however, the spin distribution is symmetric across the slab thickness, then complete cancellation of the magnetization transfer effect will occur. In this case, $K_1(z) = K_1(-z)$ and $K_2(z) = K_2(-z)$, which implies that the difference signal, $\mu_c(z) - \mu_i(z)$ is an odd function of position. Integration of this quantity across a slab centered on isocenter yields zero residual signal. However, the present inventors have found in practice that relatively good control for the magnetization transfer effect may be achieved in vivo by minimizing the slab thickness and the amplitude of the inversion pulse and by maximizing the amplitude of the inversion gradient.

Thus, in accordance with the invention, the control image may be generated either by changing the sign of the inversion gradient or by changing the sign of the frequency offset, $\omega_i$, of the inversion pulse. Due to the presence of eddy currents which result from gradient switching, it is preferable to change the sign of the frequency offset, for if one changes the sign of the inversion gradient, a different pattern of eddy currents will exist in the inversion and control images, leading to incomplete background suppression.

Another effect which may cause decreased background suppression is actual deposition of the labeled blood in the capillary beds of, for example, the brain parenchyma. This effect is the basis for a non-invasive perfusion imaging technique such as that described in the aforementioned related patent application. Fortunately, for the purposes of angiography, the magnitude of this effect is quite small, on the order of only a few percent at 1.5 Tesla.

EXAMPLE 1

Figure 4:
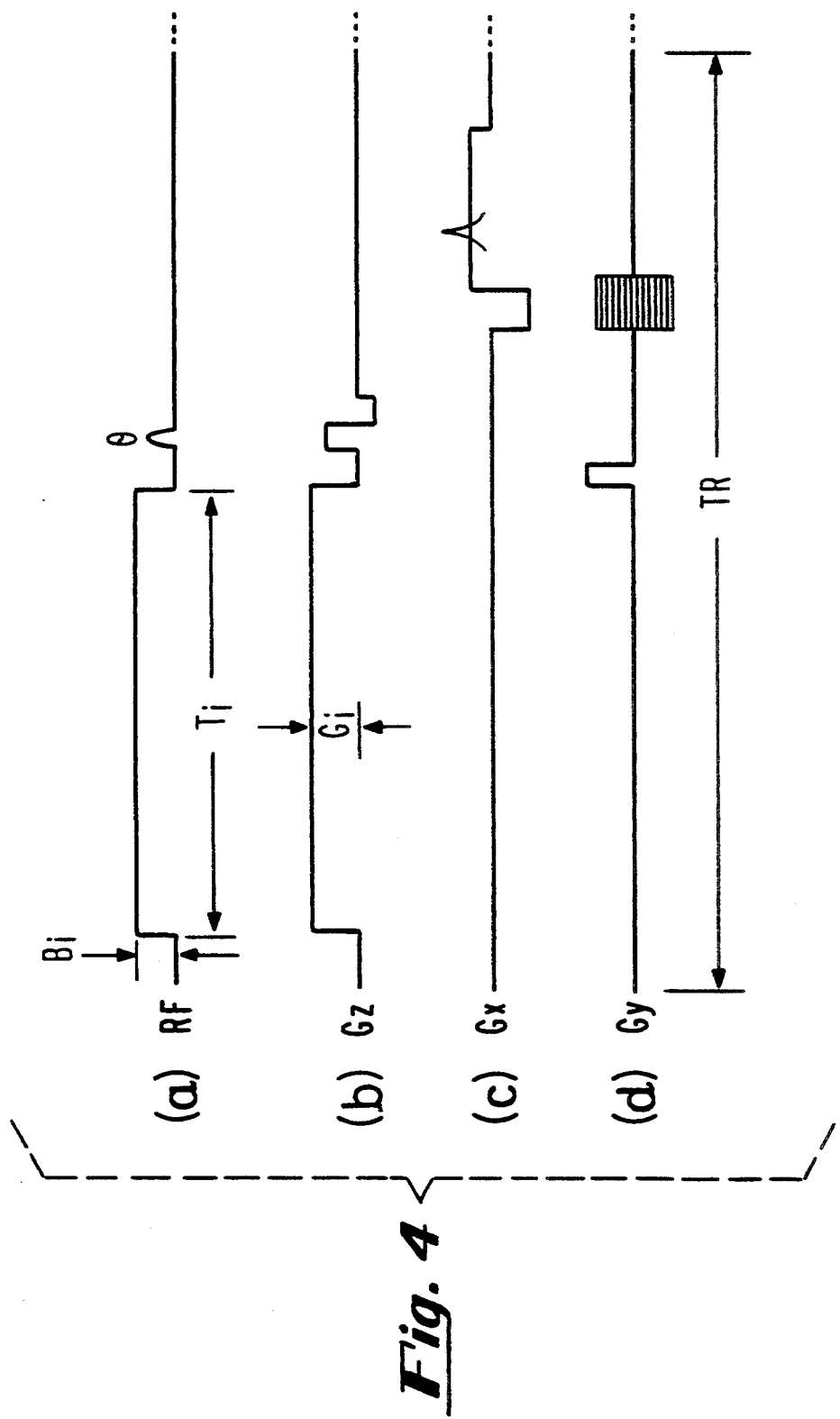
FIGS. 4(a), 4(b), 4(c) and 4(d) together illustrate a two-dimensional axial gradient-echo pulse sequence used to generate images in accordance with the embodiment of the invention described with respect to Example 1.

Experiments were conducted on a 1.5 Tesla MR imaging system (Sigma, GE Medical Systems, Milwaukee) on human volunteers. The two-dimensional axial gradient-echo pulse sequence of FIG. 4 was used to acquire inversion and control images. As shown in FIGS. 4(a) and 4(b), an off-resonance RF pulse with a constant magnitude, $B_i$, and a constant gradient pulse, $G_i$, preceded a standard imaging sequence. The frequency of the RF pulse, $\omega_i$, was chosen so that inversion always occurred through a plane 3 cm inferior to the imaging slab. The inversion RF pulse is defined by its duration, $T_i$, its strength, $B_i$, and its frequency offset, $\omega_i$. It is preferably applied in the presence of a field gradient $G_i$ which is in the slab selection direction. As shown in FIG. 4(d), a homospoil y-gradient pulse is also applied between the inversion and observation pulses to attenuate residual transverse magnetization which develops as a result of the off-resonance pulse.

Figure 5:
FIG. 5 illustrates the location of the image slab and inversion plane for use in producing an intracranial angiogram in accordance with the technique of the invention.

FIG. 5 illustrates the locations of the image slab and inversion plane used to produce angiograms of the human brain in this example. In a preferred embodiment, the image slab is 30 mm thick and the inversion plane is located 3 cm inferior to the center of the slab, which is at isocenter. As shown, the inversion plane intersects the superior portion of the internal carotid artery as it enters the cranium. A transmit/receive quadrature head coil was used to apply the RF inversion pulses and to acquire this image. In particular, the 30 mm thick image slab was excited with a field-of-view of 22 cm, $\theta=40°$, TE=5 msec and TR=100 msec. A fractional echo was used to minimize artifacts arising due to dephasing during readout. A homospoil y-gradient pulse of 4 msec duration and amplitude of 1 gauss/cm is also applied between the end of the inversion pulse and the observation pulse as illustrated in FIG. 4(d) to attenuate residual transverse magnetization created by the inversion pulse. For each slab, 256 phase encodings were performed and four signal averages were acquired, yielding an acquisition time of 1 minute and 43 seconds per image. The duration of the RF pulse was chosen to be 80 msec, corresponding to a duty cycle (RF pulse duration/TR) of 80%. Angiograms were then computed as the difference between magnitude images acquired with and without arterial inversion.

Figure 6A:
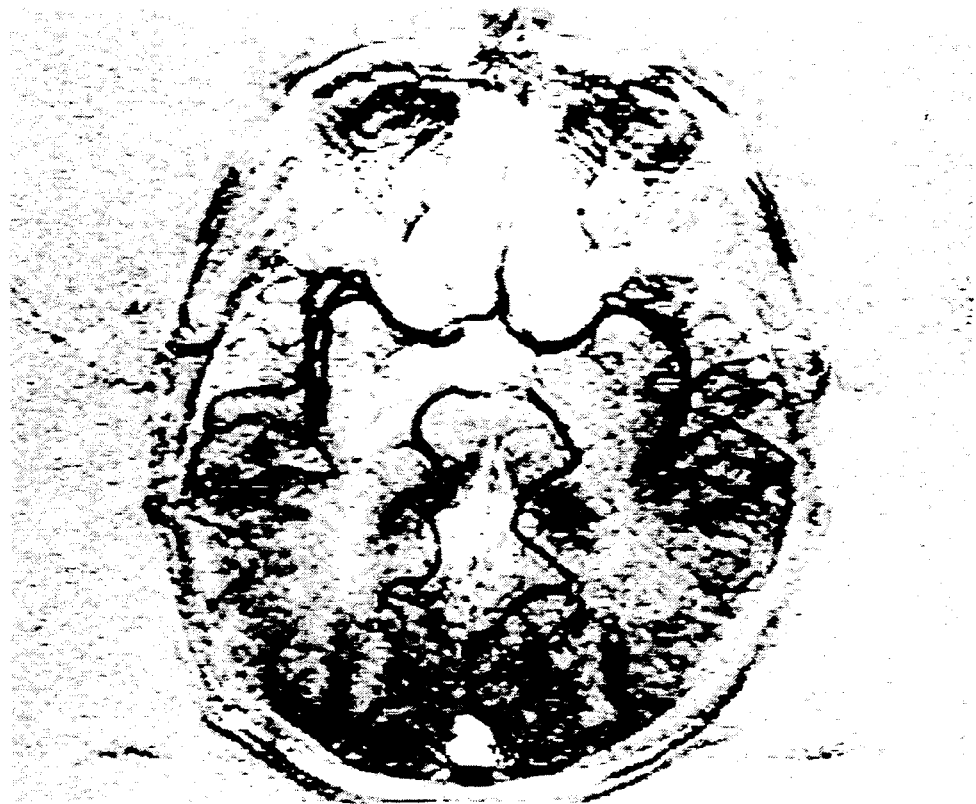
FIGS. 6(a) and 6(b) illustrate respective two-dimensional projective angiograms generated by changing the sign of the inversion gradient (FIG. 6(a)) and by changing the sign of the offset frequency of the inversion pulse (FIG. 6(b)).
Figure 6B:
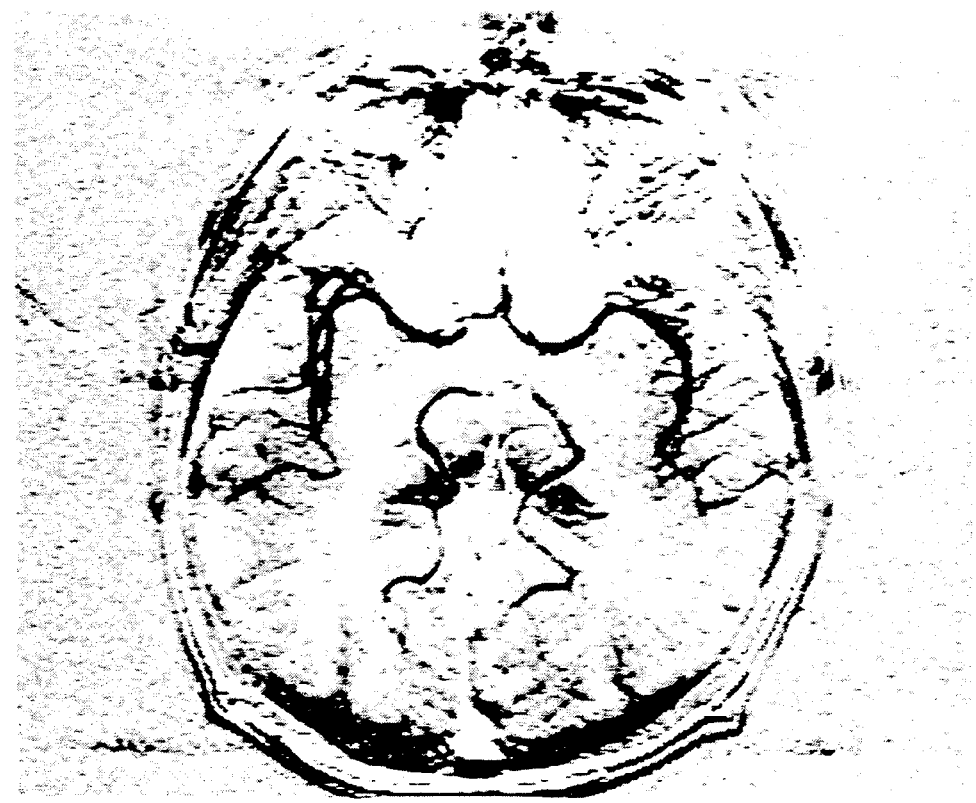

FIGS. 6(a) and 6(b) illustrate two-dimensional projective angiograms of a patient produced using the technique of the invention. These angiograms were generated by using two different methods for control. Namely, FIG. 6(a) was generated from a control image acquired by changing the sign of the inversion gradient, while the image of FIG. 6(b) was generated from a control image acquired by changing the sign of the offset frequency of the inversion RF pulse. For both angiograms in FIG. 6, the inversion gradient was 0.5 gauss/cm, the amplitude of the inversion pulse was 80 Hz, and the offset inversion frequency, $\omega_i$, was $-6400$ Hz. The total acquisition time for each angiogram in FIG. 6 was approximately 3.4 minutes.

Measurements of blood flow in the internal carotid artery (ICA) suggests that the average velocity is approximately 20 cm/sec as described by Gullberg et al. Under these conditions, pulse simulations predict that approximately 80% inversion efficiency should occur in the ICA at 80 Hz as shown in FIG. 2. There is less background suppression in FIG. 6(a) due to the unbalanced eddy currents which result from the different pattern of gradient switching. The images of FIG. 6 thus indicate that the changing of the sign of the offset frequency is a superior means of control.

FIGS. 6(a) and 6(b) also illustrate residual signal intensities near the ventricles and the occipital cortex. These are regions where one would expect to find a highly asymmetric spin distribution across the image slab and hence poor control of the magnetization transfer effect. Nevertheless, the contrast-to-noise ratio within the proximal ICA is 41 in FIG. 6(a) and 44 in FIG. 6(b).

Figure 7A:
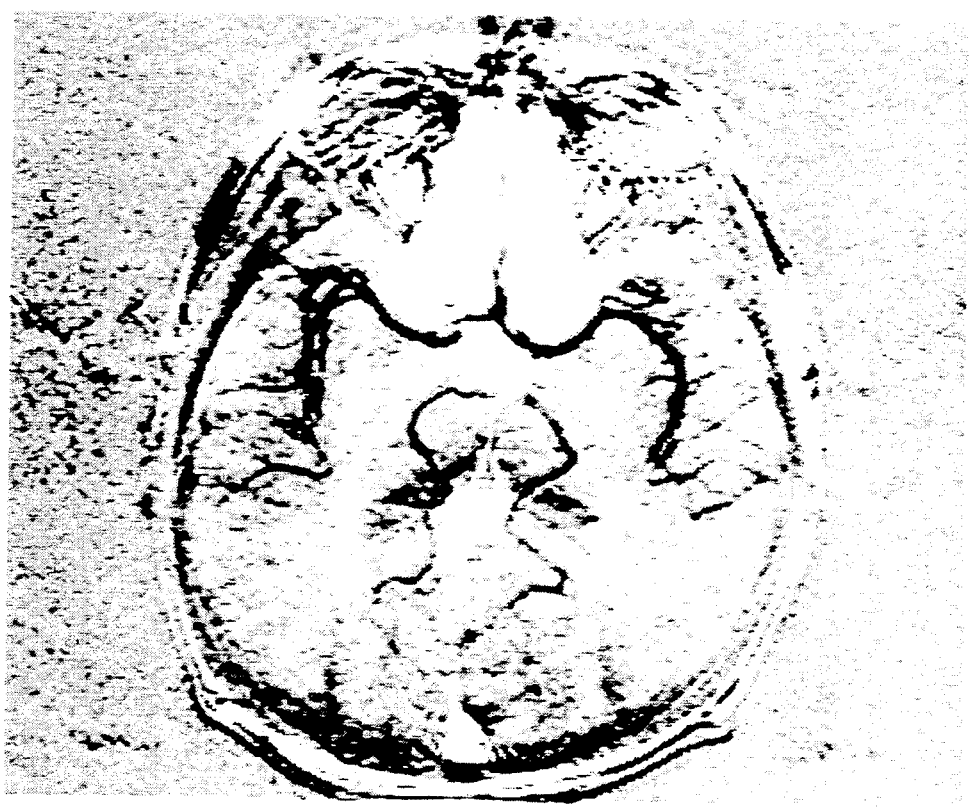
FIGS. 7(a) and 7(b) together illustrate the effect of inversion gradient strength on contrast, where $G_i = 0.25$ gauss/cm (FIG. 7(a)) and $G_i = 1.00$ gauss/cm (FIG. 7(b)).
Figure 7B:
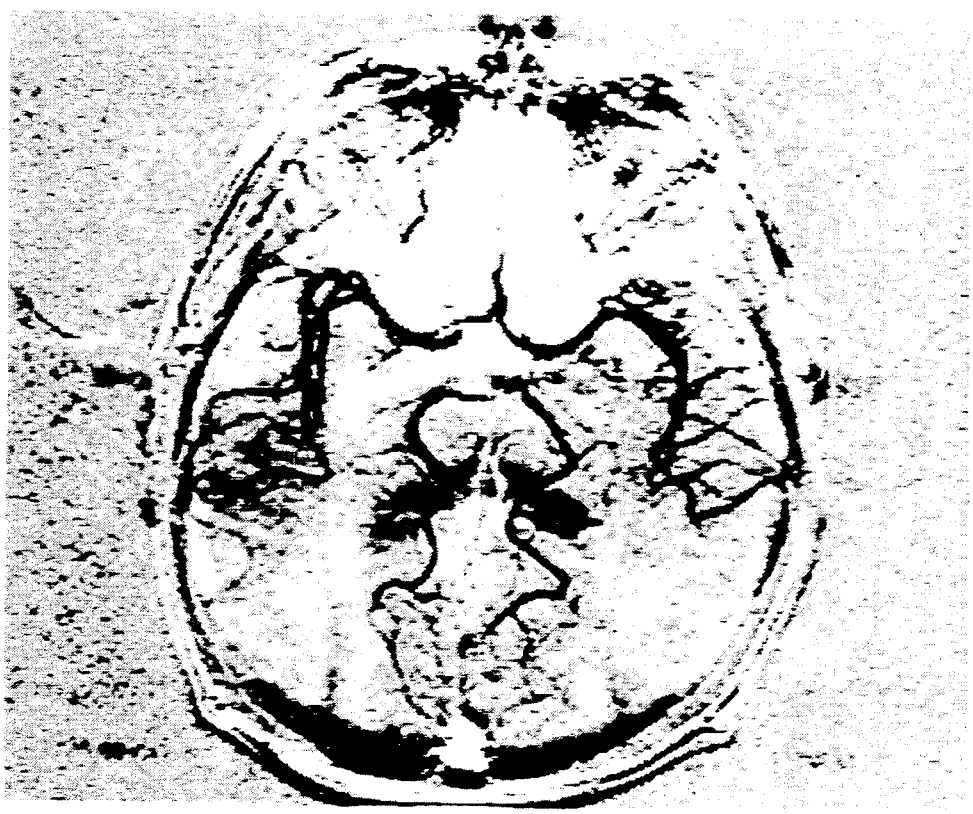

FIG. 7 illustrates the effect of inversion gradient strength on angiographic contrast in accordance with the invention. In FIGS. 7(a) and 7(b), two angiograms of a patient were generated using two different values for the inversion gradient. In FIG. 7(a), the inversion gradient $G_i$ was 0.25 gauss/cm, while in FIG. 7(b) the inversion gradient $G_i$ was 1.0 gauss/cm. For both angiograms the amplitude of the inversion pulse was 80 Hz and the total acquisition time for each angiogram was 3.4 minutes.. The plane of inversion was 3 cm inferior to the image slab in each case, and the inversion frequency, $\omega_i$, was $-3200$ Hz for FIG. 7(a) and $-12800$ Hz for FIG. 7(b). As illustrated, better visualization of the arteries is obtained at the higher gradient strength (FIG. 7(b)) due to more efficient inversion. In fact, the pulse simulations of FIG. 2 predict that the inversion efficiency for flow in the ICA under these conditions should be approximately 0.5 for FIG. 7(a) and 1.0 for FIG. 7(b). Moreover, the contrast-to-noise ratio within the proximal ICA was measured to be 29 for FIG. 7(a) and 57 for FIG. 7(b). Also, at the lower value of the inversion gradient of FIG. 7(a), the magnetization transfer effects become more prominent, as indicated by poor background suppression near the occipital cortex and the ventricles. This is expected due to greater dispersion of the effect across the slab thickness at the lower gradient strength.

Figure 8A:
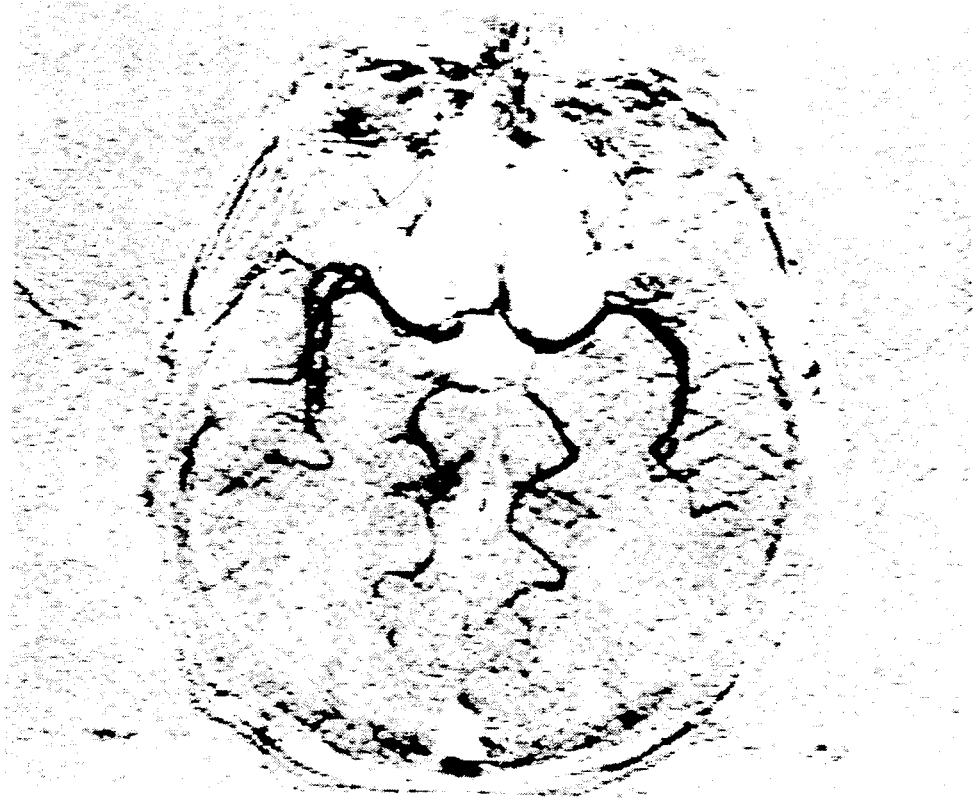
FIGS. 8(a) and 8(b) together illustrate the effect of inversion pulse amplitude on contrast, where $B_i = 40$ Hz (FIG. 8(a)) and $B_i = 120$ Hz (FIG. 8(b)).
Figure 8B:
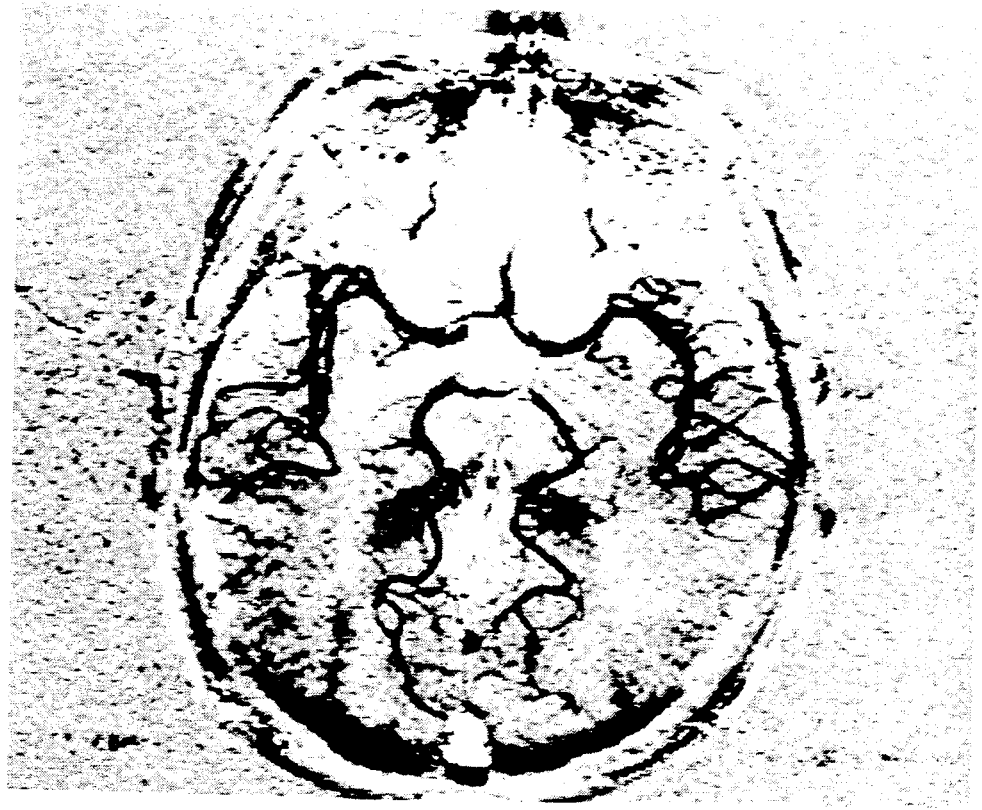

FIGS. 8(a) and 8(b) illustrate the effect of inversion pulse amplitude on angiographic contrast. Two angiograms of a patient were generated using two different values for the amplitude of the inversion pulse. In particular, the amplitude, $B_i$, of the inversion pulse was 40 Hz for FIG. 8(a) and 120 Hz for FIG. 8(b). For both angiograms, the inversion gradient was 0.25 gauss/cm and the inversion frequency, $\omega_i$, was $-3200$ Hz. The total acquisition time for each angiogram was 3.4 minutes. As shown, there is better visualization of the arteries in FIG. 8(b) than in FIG. 8(a) due to more efficient inversion of the arterial inflow. Indeed, pulse simulations predict that the inversion efficiency for flow in the ICA under these conditions should be approximately 0.5 for FIG. 8(a) and 1.0 for FIG. 8(b). The contrast-to-noise ratio within the proximal ICA was also measured to be 30 for FIG. 8(a) and 64 for FIG. 8(b). As expected, the magnetization transfer effects in the region of the occipital cortex and surrounding the ventricles are more prominent in the image generated with the higher RF (FIG. 8(b)). The average specific absorption rate for the image of FIG. 8(b) was determined to be approximately 0.2 W/kg.

The use of a steady-state inversion technique such as that described herein thus offers advantages over other techniques such as that disclosed by Dixon et al. which rely upon pulsed inversion. Specifically, one may shorten the TR interval in accordance with the invention and use fast scan approaches to imaging without the complications of cardiac gating. In addition, the inversion pulse is insensitive to variations in blood flow as long as the conditions of Equation 1 are satisfied. Also, since the present invention does not use shaped pulses to label blood flow as in SIR techniques, no optimized pulse shapes need to be computed and hence the demands on the RF amplifier hardware are less stringent. Moreover, while the motion of the spins during the inversion pulse is a source of error for techniques which rely upon spatially selected pulses (SIR), the present invention actually relies upon spin motion during the pulse for inversion to occur. Yet another advantage of the invention is the fact that all moving spins are inverted at the same location, which may be placed quite close to the imaging region. This reduces the loss of contrast due to $T_1$ relaxation of the labeled spins. Also, by using a single coil to apply the inversion and observation pulses, the blood supply may be inverted very close to the imaging slab so as to minimize transit time effects.

The amount of arterial inflow which is inverted, which should be proportional to angiographic contrast, is directly proportional to the duty cycle of the inversion pulse. For this reason, it is important to use as large a duty cycle as possible in accordance with the invention. In order to minimize the RF signal magnitude necessary for inversion it is also desired to reduce the amplitude of the inversion gradient. However, as the strength of the inversion gradient is decreased, failure to control for magnetization transfer effects leads to poorer background suppression in regions where high spin asymmetry across the imaging slab exists. Fortunately, the present inventors have found that, in practice, this effect is relatively small and does not significantly degrade the quality of the angiograms. Also, by using a single head coil to apply the pulses and by using small inversion gradients, it has been possible to keep the average specific absorption rate well below FDA limits for human head exposures using the techniques of the invention.

Coronary Angiography Using Transport-Induced Adiabatic Fast Passage

Theory

The MRA technique described above with respect to Example 1 has been applied to coronary vasculature by inverting the blood at an arbitrary location in the imaging volume proximal the heart. In particular, the principle of transport-induced adiabatic vast passage inversion has been used to label blood flow in the coronary vessels. The basic technique is very similar to that described above with respect to intracranial angiography except that, as will be described below, a "localizer" image is first taken in order to determine the geometry of the patient's heart.

For coronary angiography, as with intracranial angiography, a constant magnitude, transverse RF field, $B_i$, is applied in the presence of a magnetic field gradient, $G_i$, so as to generate adiabatic inversion of spins which have a component of velocity in the direction of the gradient. Thus, as described above with respect to Equation 1, if a spin moves too slowly, relaxation effects dominate and inversion does not occur, while conversely, if a spin moves to rapidly, incomplete inversion will occur because the sweep becomes non-adiabatic. However, computer simulations performed by the present inventors revealed that the RF amplitude necessary for 90% inversion of spins is relatively low. The inversion efficiency is a function of a dimensionless parameter, $\beta$, which is defined as:

$$\beta = (\gamma B_i)^2/(\gamma G_i v), \qquad \text{Equation 9}$$

where $\gamma$ is the gyromagnetic ratio and $B_i$ is the amplitude of the inversion pulse. Computer simulations have also revealed that approximately 90% inversion is achieved when $\beta$ is only two. As a result of this, it is possible to use relatively low amplitude RF pulses to effect inversion, thereby reducing the power deposition of the experiment.

As described above with respect to Equation 3, the off-resonance inversion pulse defines a plane of inversion. Any spin which moves through this plane will experience adiabatic inversion as long as its velocity satisfies the conditions of Equation 1. The distance between the inversion plane and the isocenter is also given by Equation 3 above. The directional sensitivity of the inversion pulse is thus completely under operator control simply through choice of gradient direction.

Figure 9A:
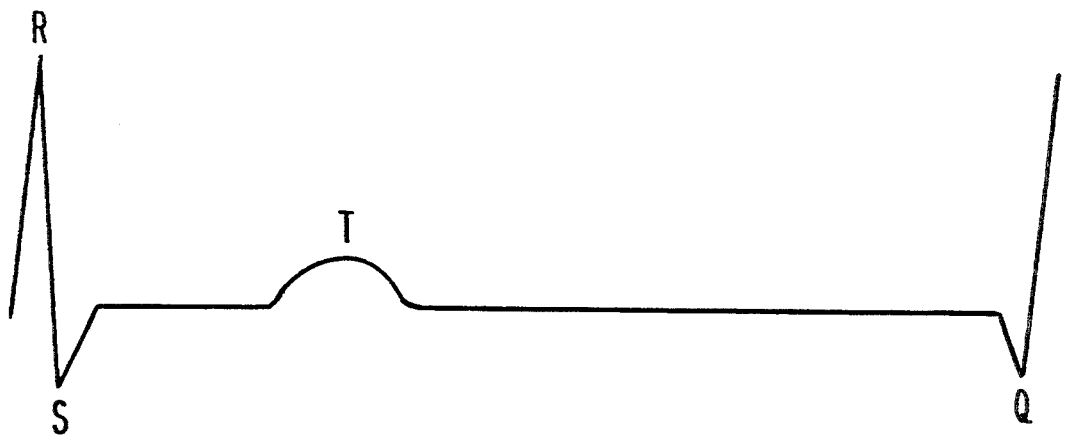
FIGS. 9(a), 9(b) and 9(c) together illustrate the time courses of ventricular ejection and coronary blood flow during the cardiac cycle.
Figure 9B:
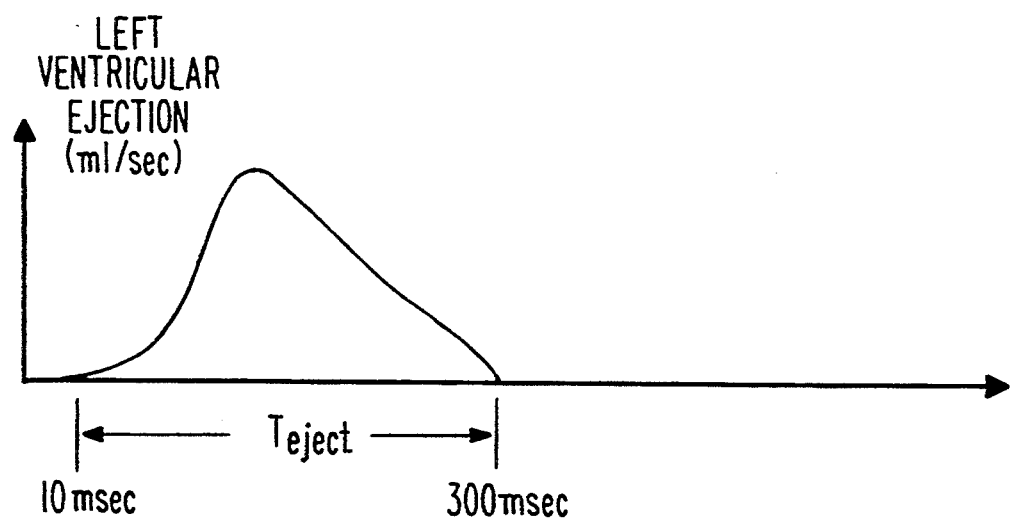
Figure 9C:
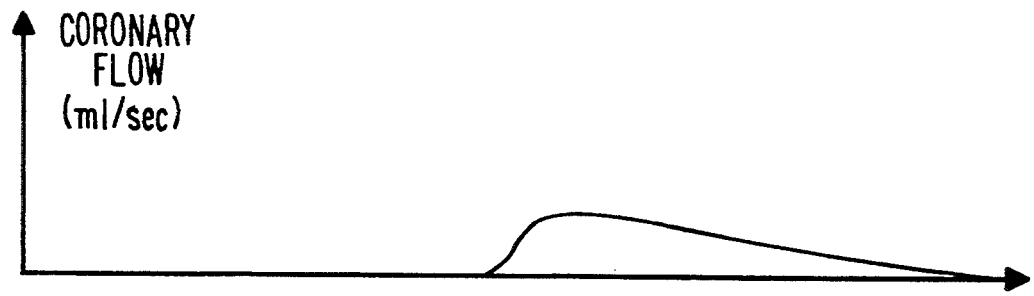

FIGS. 9(a)–9(c) illustrate how transport-induced adiabatic fast passage pulses may be used to label blood flow in the coronary arteries. As shown in FIGS. 9(a) and 9(b), relative to the R wave of the electrocardiogram (0 msec), the ventricular ejection period lasts from approximately 10 msec to 300 msec during systole. As shown in FIG. 9(c) coronary blood flow during this period is negligible due to myocardial contraction. As will be appreciated by those skilled in the art, by applying the inversion pulse during the period of ventricular ejection ($T_{eject}$), it is possible to effectively label all of the cardiac output. During diastole, labeled blood which is ejected from the left ventricle of the heart flows into the coronary arteries at the base of the aorta. Thus, by timing data acquisition to occur at the end of diastole, one may observe the labeled blood in the coronary arteries. Subtraction of images acquired with and without the inversion pulse yields a coronary angiogram.

Such selective labeling of the ventricular ejection period is advantageous for a number of reasons. First, it makes it possible to label the coronary blood flow with a shorter duration pulse, thereby reducing the duty cycle of the RF and the power deposition as compared with the embodiment described with respect to Example 1. In addition, it reduces errors which arise from the fact that the inversion pulse, as a result of the gradient geometry, inevitably labels blood flow in the left atrium. Labeled blood in the left atrium enters the left ventricle and causes a background signal to appear in the left ventricle in the angiogram. This "cavity effect" makes it harder to see the coronary vessels in a projection angiogram. By shortening the duration of the inversion pulse and applying it only during ventricular ejection during systole, the "cavity effect" may be minimized. Moreover, the use of a shorter inversion pulse also reduces the amount of magnetization transfer to spins in the image slab. Magnetization transfer effects have been found by the present inventors to be an error in this form of projective angiography; therefore, by reducing the degree of magnetization transfer, use of a shorter inversion pulse improves the quality of the angiograms.

EXAMPLE 2

Experiments were conducted on a 1.5 Tesla MR imaging system (Signa, GE Medical Systems, Milwaukee) on human patients. The patients were placed in the bore of the magnet and a set of gated "localizer" images of the heart were acquired in approximately five minutes. These "localizer" images enabled the operator to determine from the parameters on the localizer image where to put the imaging plane and where to put the inversion plane. In particular, the "localizer" images allowed for accurate localization of the left ventricle and aortic valve and allowed the frequency offset of the inversion pulse to be determined using Equation 3. A frequency was chosen such that blood flow in the superior portion of the left ventricle would undergo inversion. In addition, the localizer images were used to determine the geometry of the image slab. In general, an image plane is desired which transects the aortic valve on its longitudinal axis so as to include the entire curve of the aorta, while an inversion plane is desired which is approximately one centimeter inferior (intraventricle) with respect to the aortic valve. Also, the image slab preferably covers the entire myocardium.

The two-dimensional gated coronal gradient-echo pulse sequence of FIG. 10 was then used to acquire inversion and control images and to form coronary angiograms using transport induced adiabatic fast passage. In particular, a constant off-resonance RF pulse was applied in the presence of a constant inversion gradient in the frequency encoding direction as illustrated in FIGS. 10(b) and 10(e) prior to application of a standard two-dimensional gradient-echo imaging sequence as illustrated in FIGS. 10(b)-10(e). The inversion pulse was applied during ventricular ejection to label the ventricular outflow, and the image was later acquired during diastole, by which time the labeled blood had entered the coronary arteries. The frequency of the inversion pulse, $\omega_i$, was chosen so that inversion always occurred through a plane perpendicular to the z-axis and was positioned one centimeter inferior (intraventricle) to the aortic valve. The inversion pulse duration was 240 msec (i.e., $T_i$=240 msec) and it began 100 msec after the R wave trigger as illustrated in FIGS. 10(a) and 10(b). The amplitude of the inversion pulse was 60 Hz and the amplitude of the inversion gradient was 0.2 gauss/cm. Data acquisition then occurred 550 msec after the R wave trigger as illustrated in FIGS. 10(b)-10(e).

A transmit/receive quadrature body coil was used to apply the inversion RF pulse as well as the imaging pulse, and a 40 mm thick slab over the myocardium was excited with a field-of-view of 24 cm, $\theta$=90° and TE=5 msec. A fractional echo was used to minimize artifacts arising due to dephasing during readout. A homospoil y-gradient pulse of 4 msec duration and amplitude of 1 gauss/cm was also applied between the end of the inversion pulse and the observation pulse to attenuate residual transverse magnetization created by the inversion pulse in the preferred embodiment (FIG. 10(c)). Four signal averages were acquired for inversion and control images yielding a total acquisition time of approximately 14 minutes. The average specific absorption rate of this experiment was 0.3 W/kg, which is below the FDA limit for human whole body exposures. Angiograms were then computed as the difference between magnitude images acquired with the amplitude of the inversion pulse set to 60 Hz and 0 Hz, respectively.

Figure 11:
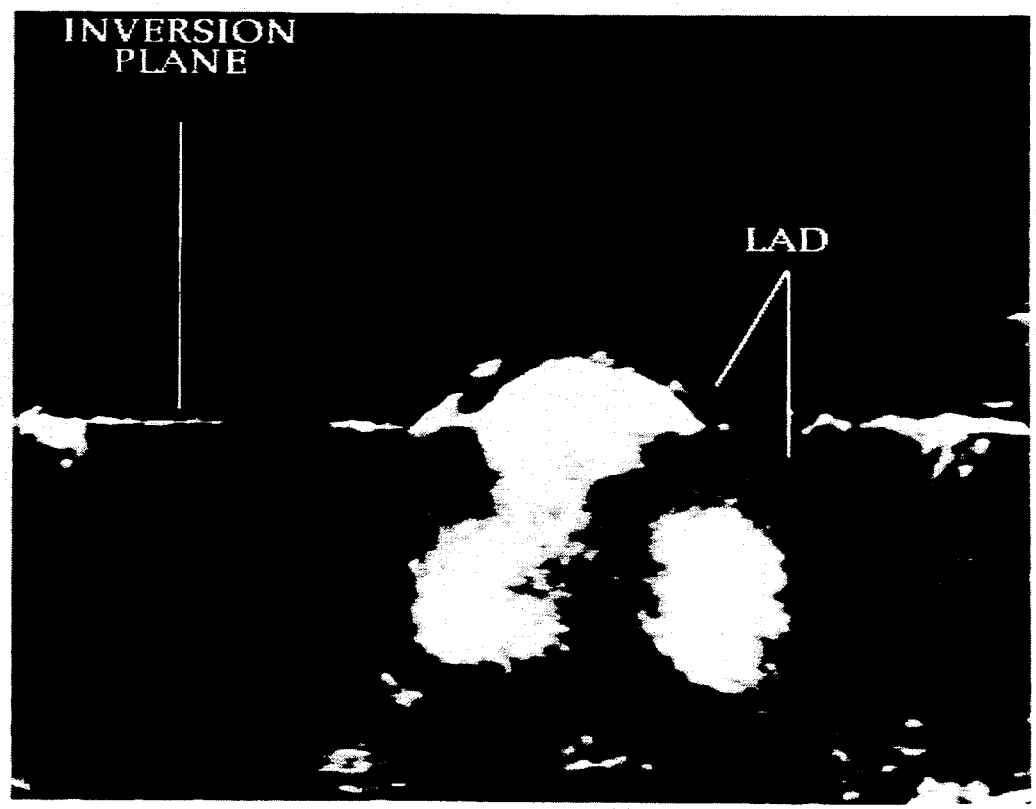
FIG. 11 illustrates a coronary angiogram produced in accordance with the invention whereby the bright horizontal band in the image indicates the geometry of the inversion plane.

FIG. 11 illustrates an angiogram produced in accordance with the technique of the invention. The bright horizontal band in FIG. 11 indicates the geometry of the inversion plane. The left anterior descending (LAD) branch of the left main coronary artery is also labeled. Blood flow in the proximal left coronary artery is clearly labeled by the inversion pulse, while blood within the left ventricle is also labeled due to residual cavity effects. Unfortunately, in FIG. 11 this makes it difficult to observe the course of the left coronary artery as it descends in front of the left ventricle.

Example 2 demonstrates that coronary blood flow may be labeled through use of transport-induced adiabatic fast passage inversion pulses. As noted above with respect to Example 1, use of this technique in a steady-state fashion in a human brain revealed the presence of magnetization transfer effects which lead to incomplete background suppression. However, the present inventors have found that these effects are negligible in the coronary circulation, which is most likely due to the fact that the duty cycle of the inversion pulse was only about 20% in Example 2, in contrast to duty cycles of 80% or more which were used in the cerebral applications described above with respect to Example 1.

Improvements in the quality of the angiograms in Example 2 may be achieved by pursuing alternate geometries to better visualize the coronary vessels. In addition, more careful timing of the inversion pulse should further minimize cavity effects. Specifically, it may be desirable to only label the latter half of the systolic ejection since most of the blood which enters the coronary circulation is ejected during this time period. The use of higher resolution flow compensation gradient waveforms, projection imaging methods, single-shot imaging (echoplanar imaging) and/or respiratory compensation should also improve the quality of the angiograms of Example 2 in accordance with the invention.

Quantitative MR Flow Measurement Using Pulsed Adiabatic Inversion

Theory

By using the MR angiography techniques described above with respect to Examples 1 and 2 in conjunction with the tissue perfusion technique described in the aforementioned U.S. patent application and a technique for MR blood flow measurement, a comprehensive MR imaging system for imaging the heart, the brain, the kidney, the liver and other major tissues and organs may be accomplished nonintrusively using magnetic resonance. In order to fulfill the requirements of such a comprehensive imaging system, the present inventors have further developed a technique for measuring flow velocity using constant amplitude RF pulses in the presence of a magnetic gradient to adiabatically invert spins which move in the direction of the gradient as in the techniques described above and by Williams et al. in the aforementioned U.S. patent application and paper.

Figure 12:
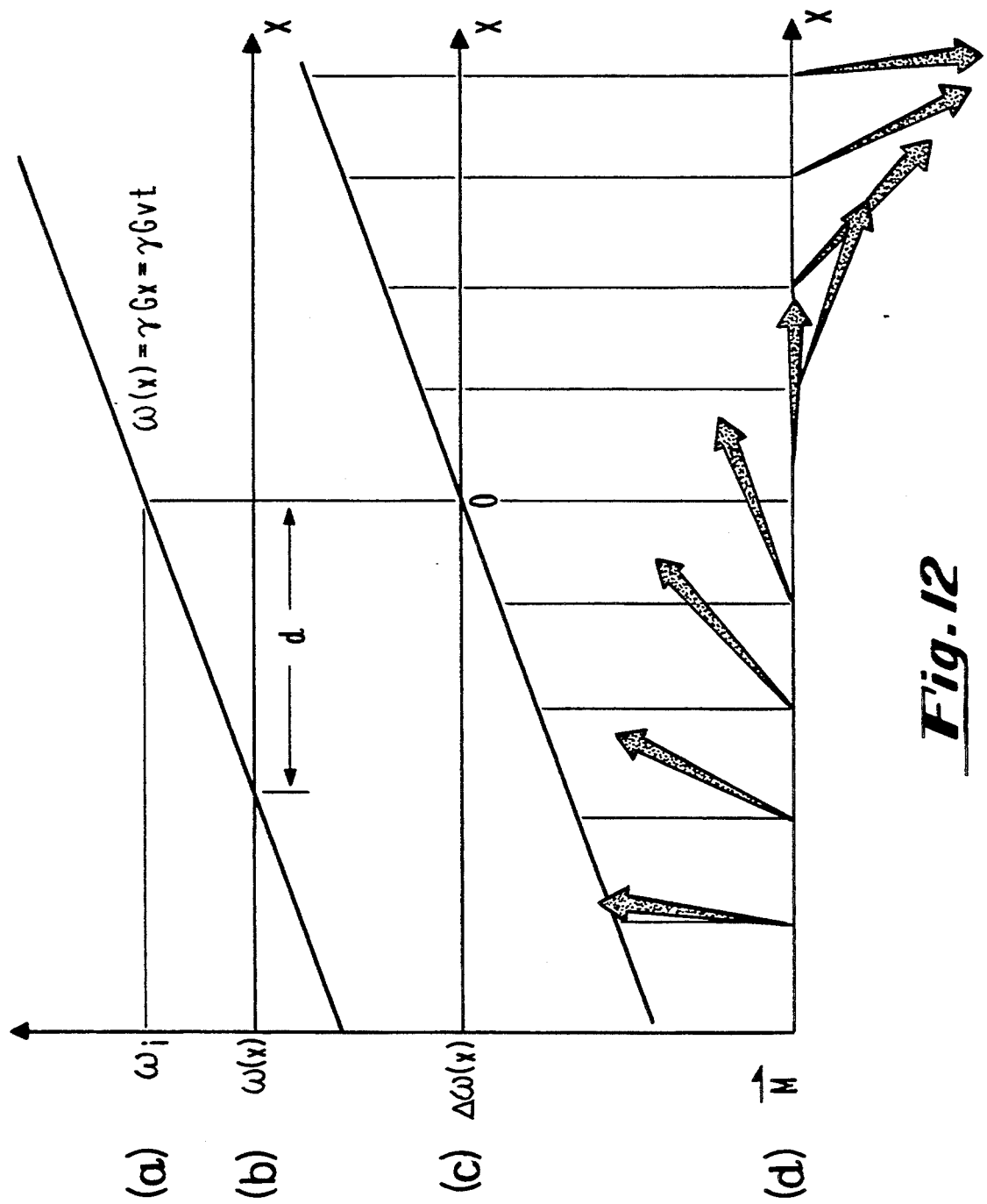
FIG. 12 illustrates how the location of the inversion plane depends on the inversion gradient $G_i$ and the offset frequency $\omega_i$.

The theory of MR flow measurement in accordance with the invention is similar to that given above for MR angiography. In particular, as described above with respect to FIG. 1, a spin which moves through a linear magnetic field gradient at constant velocity in the presence of an off-resonance RF pulse undergoes adiabatic fast passage by virtue of its motion. FIG. 12 illustrates the effect of a constant RF pulse on a spin moving through a gradient at constant velocity. As shown in FIG. 12, as the spin moves through the gradient, G, it undergoes a frequency sweep which has a rate determined by the velocity of the spin and the strength of the gradient. If the sweep rate is slow enough or if the strength of the RF pulse is large enough, the magnetization will follow the effective field, $B_{eff}$, and adiabatic inversion will occur. In short, adiabatic inversion of the liquid will occur if its velocity satisfies Equation 1. As noted above, this approach to spin labeling differs fundamentally from approaches using spatially selective pulses in that it relies upon motion of the spins during the pulse to effect inversion.

The inversion gradient defines an "inversion plane" perpendicular to the gradient whose location d is given above by Equation 3. However, in this embodiment, application of intermittent pulses of RF in the presence of a gradient results in "bands" of inversion in the fluid which propagate downstream from the site of inversion. The length, $\Delta$, of an inversion band is given by:

$$\Delta = v \cdot T_i, \quad \text{Equation 10}$$

where Ti is the duration of the inversion pulse. As will be described below, in a pulsed steady-state imaging experiment a characteristic banding pattern is established in the fluid.

Figure 13A:
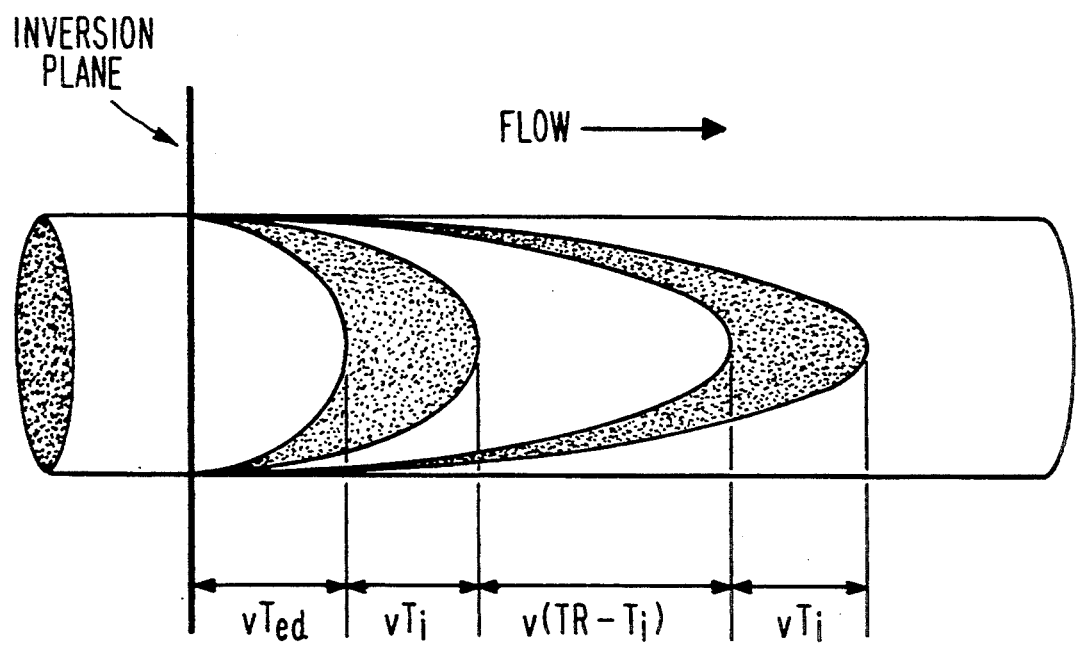
FIG. 13(a) illustrates a typical banding pattern established in a flowing liquid by a series of inversion pulses in accordance with the invention, where $T_i$ is the duration of the inversion pulse, $T_{ed}$ is the time between the end of the inversion pulse and the center of the echo, and TR is the repetition time.
Figure 13B:
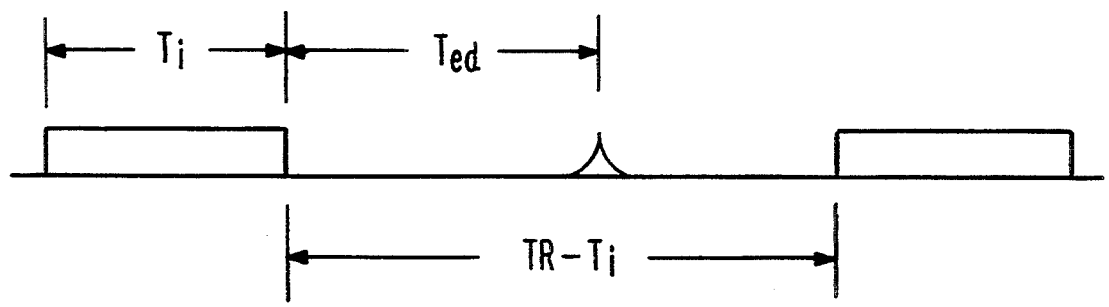
FIG. 13(b) illustrates the RF pulse sequence for forming the bands of FIG. 13(a).

FIG. 13(a) illustrates a typical banding pattern established in a flowing liquid by a train of RF pulses as illustrated in FIG. 13(b). Each band corresponds to a specific timing interval in the pulse sequence of FIG. 13(b), where $T_i$ is the duration of the inversion pulse, $T_{ed}$ is the time interval between the end of the inversion pulse and the center of the echo, and TR is the repetition time. Measurement of the length of the bands allows calculation of the average velocity over a known time interval from Equation 10. By gating such a pulse sequence to the cardiac cycle, it is possible to make make numerous quantitative in vivo measurements of flow velocities in a single cardiac cycle and to average the measured velocities over the cycle.

EXAMPLE 3

An experiment was conducted on a simple phantom and on humans using a 1.5 Tesla GE Signa imaging system.

Tube Phantom Studies

Figure 14:
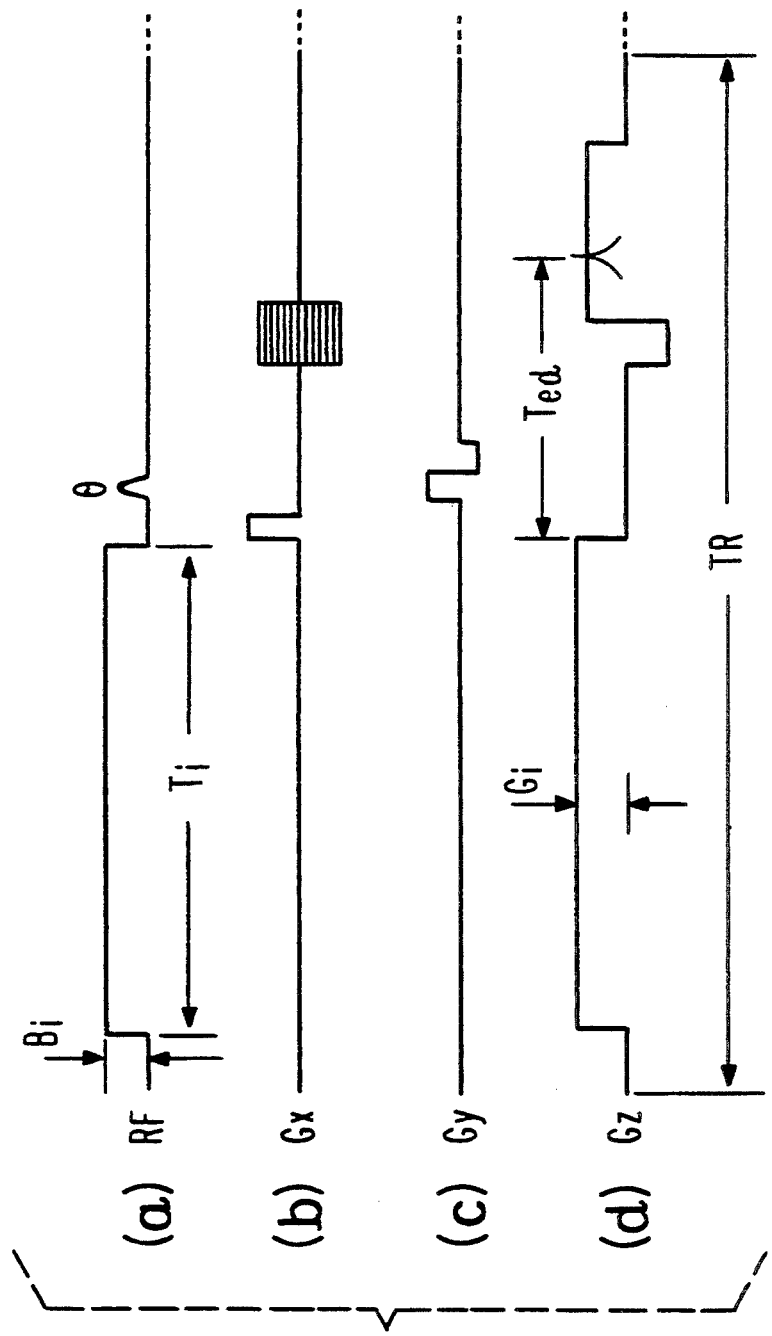
FIGS. 14(a), 14(b), 14(c) and 14(d) together illustrate a two-dimensional coronal gradient-echo pulse sequence used to make ungated flow measurements in accordance with the invention, whereby the inversion pulse is defined by its duration, $T_i$, its strength, $B_i$, and its frequency offset, $\omega_i$.

As illustrated in FIG. 14, an ungated two-dimensional coronal gradient echo pulse sequence was used to implement the technique of the invention to study flow in a simple phantom. In FIG. 14(a), a constant magnitude, off-resonance inversion RF pulse defined by its duration, $T_i$, its strength, $B_i$, and its frequency offset, $\omega_i$, was applied in the presence of a field gradient $G_i$ which in the sequence of FIG. 14 is in the z-direction (FIG. 14(d)). A homospoil gradient pulse in the x-direction having an amplitude of 1 gauss/cm and a width of 4 msec was also applied (FIG. 14(b)) after the inversion pulse to attenuate residual transverse magnetization as a result of the off-resonance pulse. A standard imaging sequence was then applied.

A transmit/receive quadrature birdcage head coil was used for applying the inversion pulse and acquiring the image. Magnitude, coronal images were acquired with $\theta = 30°$, TE=6 msec, TR=80 msec, a field-of-view (FOV) of 16 cm, and a slice thickness of 3 mm. A fractional echo was also used to suppress flow artifacts arising from dephasing during readout. The phantom consisted of 0.5 inch diameter Tygon tubing through which tap water was driven in the +z direction by a varistaltic pump. The slice location was chosen to be at the center of the tube. The flow rate was determined to be 520 ml/min by collecting a volume over a known time interval.

Figure 15C:
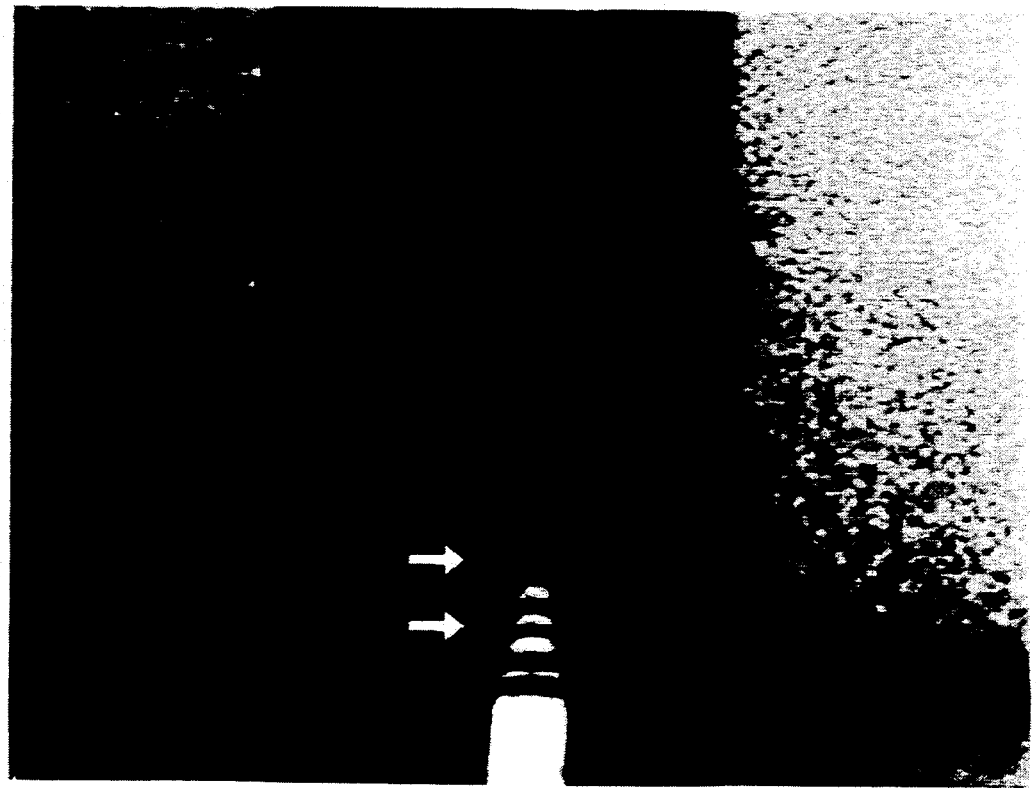
FIGS. 15(a), 15(b), 15(c) illustrate the magnitude of gradient-echo images of water flowing through ½ inch tubing, where $B_i$=20 Hz, 40 Hz, and 80 Hz, respectively. As illustrated, bright inversion bands are formed at the higher RF frequencies.
Figure 15A:
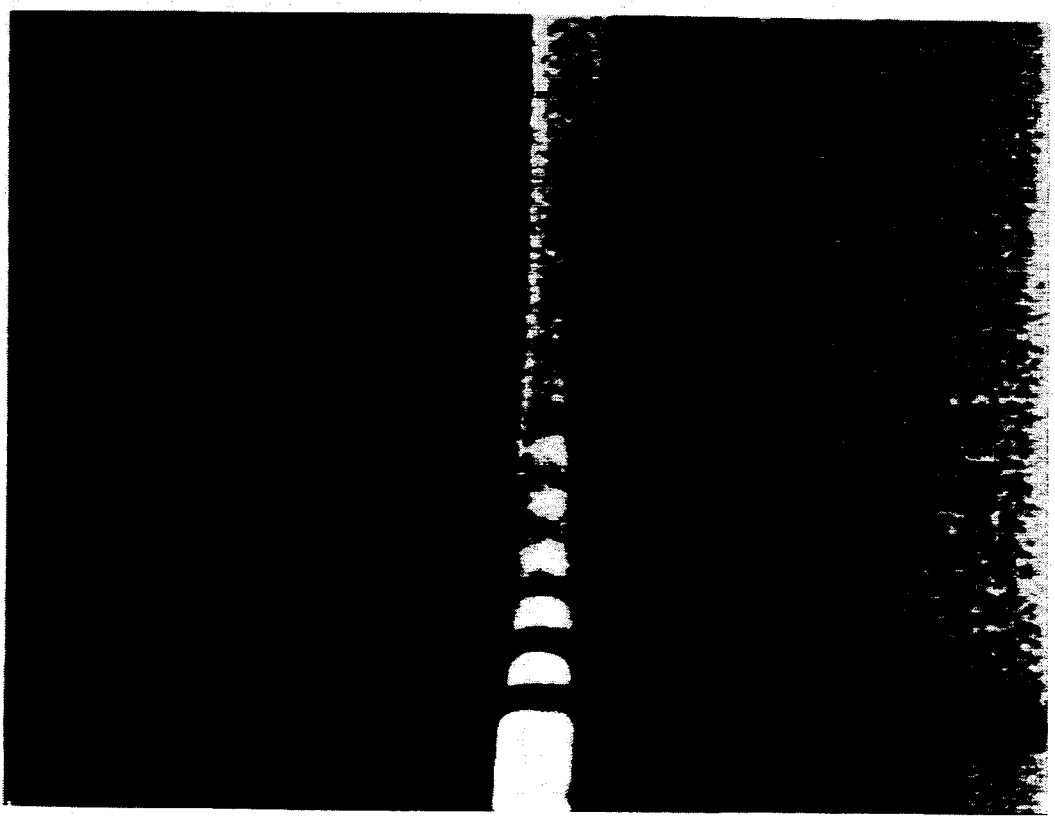
Figure 15B:
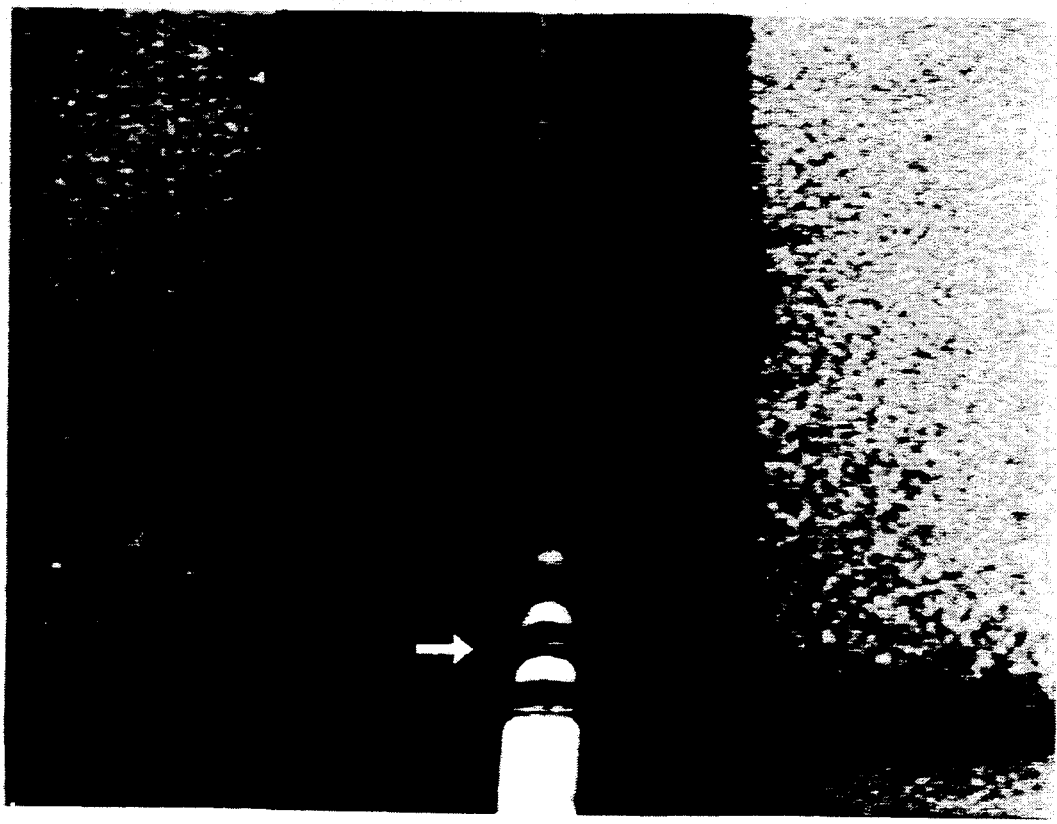

FIGS. 15(a)–15(c) illustrate typical banding patterns produced by the pulse sequence of FIG. 14 for three different strengths of the inversion pulse: $B_i=20$, 40, and 80 Hz, respectively. In particular, FIGS. 15(a)–15(c) illustrate magnitude gradient echo images of water flowing through ½ inch diameter tubing at a flow rate of 520 ml/min in the +z direction, corresponding to a peak velocity of about 14 cm/sec. A 40 msec inversion pulse was applied 2554 Hz below resonance in the presence of a z-gradient of 0.1 gauss/cm. The inversion pulse was thus characterized by $G_i=0.1$ gauss/cm, $\omega_i=-3000$ Hz and $T_i=40$ msec. The echo delay, $T_{ed}$, was chosen to be 10 msec. As shown in FIGS. 15(a)–15(c), as the RF signal intensity increases, the degree of inversion increases, reflected by the development of bright inversion bands (at the arrows) at the higher magnitude images of FIGS. 15(b) and 15(c). Pulse simulations perfoiled by the present inventors predicted that the inversion efficiency, $\alpha$, is as defined in Equation 2, where $M_0$ and $M_z$ were at the z-magnetizations before and after passage through resonance and should be 0.50, 0.90 and 0.95 for inversion strengths of 20, 40, and 80 Hz, respectively. Values for $\alpha$ were measured from the images of FIGS. 15(a)–15(c) by computing the ratio of the image intensity in the center of the first inversion band to the image intensity just upstream from the inversion plane. The values obtained were 0.38, 0.76 and 0.86 for FIGS. 15(a), 15(b), and 15(c) respectively. As shown, the intensity of the inversion bands decreases due to T1 relaxation as the flow propagates downstream, with the inversion bands of FIG. 15(c) lasting longer than those of FIG. 15(b) due to more complete inversion. This effect may, in part, explain why the measured values for $\alpha$ are somewhat lower than the predicted values.

Figure 16:
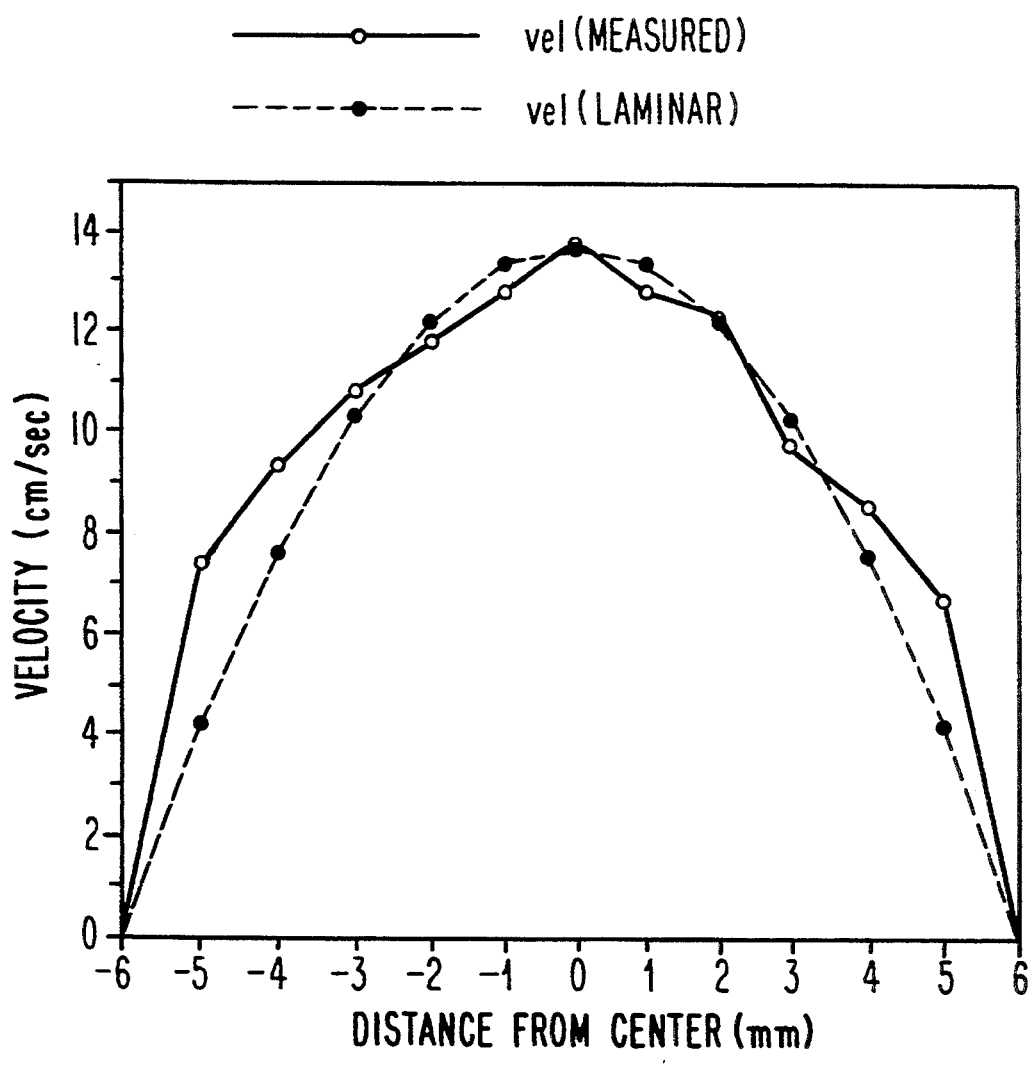
FIG. 16 illustrates the measured (solid) and predicted (dashed) values for velocity versus position across the lumen for steady flow in a ½ inch tube phantom as illustrated in FIG. 15.

In FIG. 16, the measured (solid) and predicted (dashed) values for the flow velocity calculated from FIG. 15(c) are plotted versus distance across the lumen for a steady flow in a ½ inch diameter tube phantom. The flow velocity was determined by measuring the thickness of the first inversion band and dividing by the time interval $T_i$. Also plotted is the laminar flow profile which corresponds to the measured volumetric flow rate and tube diameter. The Reynold's number defined by the peak velocity and tube diameter in the illustrated example is approximately 1700, indicating that laminar flow should exist. Excellent agreement between predicted and measured values is obtained except in the region where the velocity is low, such as near the vessel wall.

The images of FIG. 15 illustrate the usefulness of the technique of the invention for observing the dynamic aspects of flow. As shown, as the spin boluses propagate downstream from the inversion plane, contrast between bands is lost. This loss of contrast results from the effects of T1 relaxation of the spins as they travel downstream and mixing which occurs as a result of diffusion. This spins immediately next to the vessel wall, which are moving too slowly to undergo inversion, are simply saturated. As they flow downstream, they recover via T1 relaxation over a shorter distance than the more rapidly flowing spins, and hence are relatively bright. The fact that they retain higher signal down the length of the tube implies that little mixing between layers is occurring, as one would expect for laminar flow.

Human Studies

Figure 17:
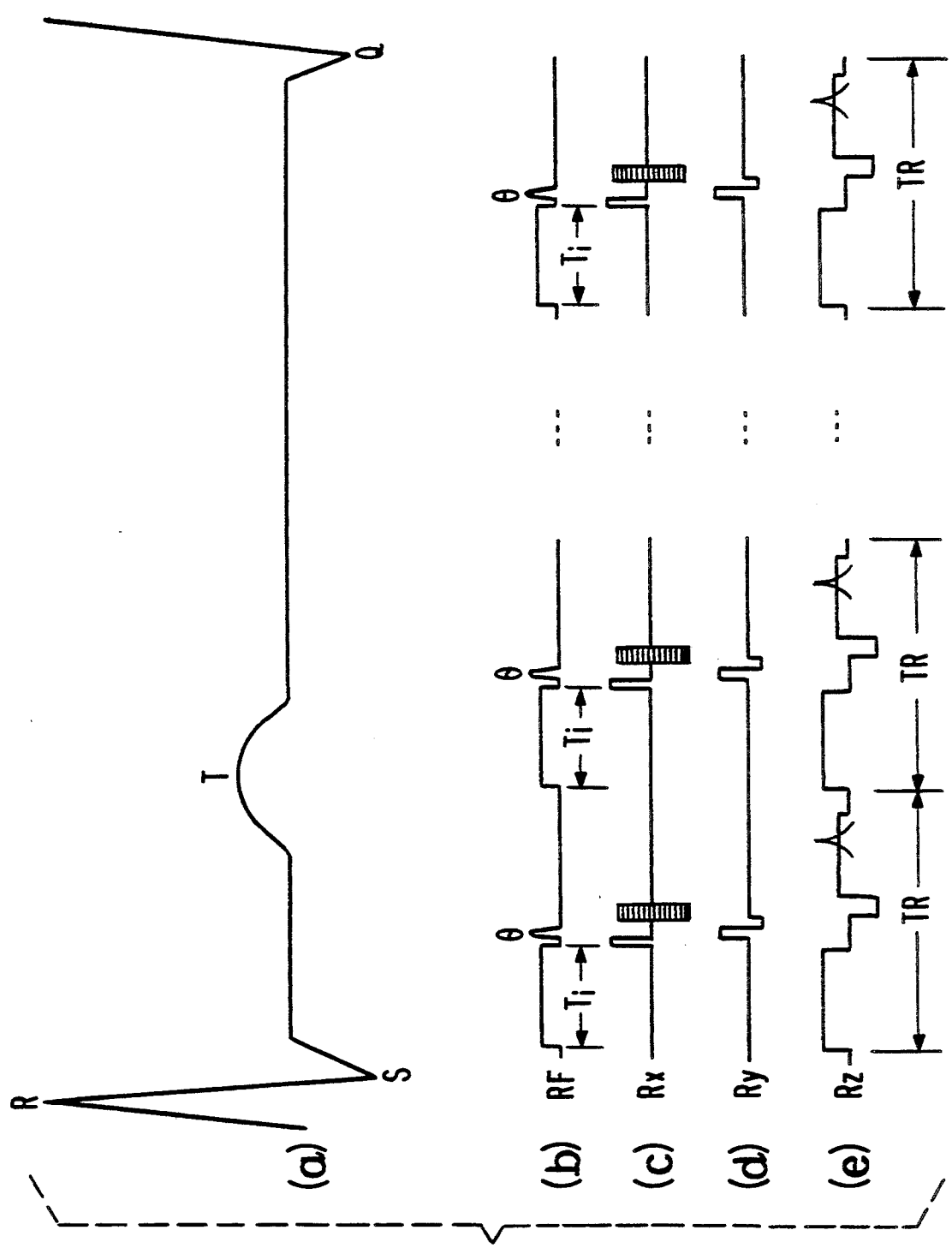
FIGS. 17(a), 17(b), 17(c), 17(d) and 17(e) together illustrate a two-dimensional gated pulse sequence used to make in vivo flow measurements in accordance with the invention, whereby the inversion flow-tagging pulse precedes each phase encoding.

Cardiac gated flow velocity waveforms were acquired from the internal carotid artery (ICA) of patients using the modified Cine pulse sequence of FIG. 17. FIG. 17 illustrates a two-dimensional gated pulse sequence used to make in vivo flow measurements, whereby after the R wave trigger, a series of images are acquired, each corresponding to a different time point of the cardiac cycle. As shown in FIG. 17(e), the repetition time, TR, was chosen to be as small as possible in order to maximize the number of observed cardiac phases Magnitude coronal images were formed with $\theta = 30°$, TE=5 msec (a fractional echo was used), a 16 cm FOV, and a slice thickness of 12 mm. A constant off-resonance RF pulse (FIG. 17(b)) in the presence of a z-gradient (FIG. 17(e)) preceded each observation pulse.

Flow velocities were then calculated by measuring the distance between the plane of inversion and the trailing edge of the first inversion band and dividing by the time between the end of the inversion pulse and the center of the echo, the echo delay $T_{ed}$ as illustrated in FIG. 14. These measurements yielded average values for the velocity of the spins during the time interval $T_{ed}$. However, those skilled in the art will appreciate that the average velocity could also be calculated by measuring the length of the first inversion band and dividing by the time interval $T_i$. Each gated image therefore contains information about the velocity during more than one part of the cardiac cycle.

Figure 18A:
FIGS. 18(a) and 18(b) illustrate gated magnitude gradient-echo images of the internal carotid artery of a human patient using the pulse sequence of FIG. 17 for the systolic portion of the cardiac cycle (FIG. 18(a)) and the diastolic portion of the cardiac cycle (FIG. 18(b)).
Figure 18B:
Figure 19:
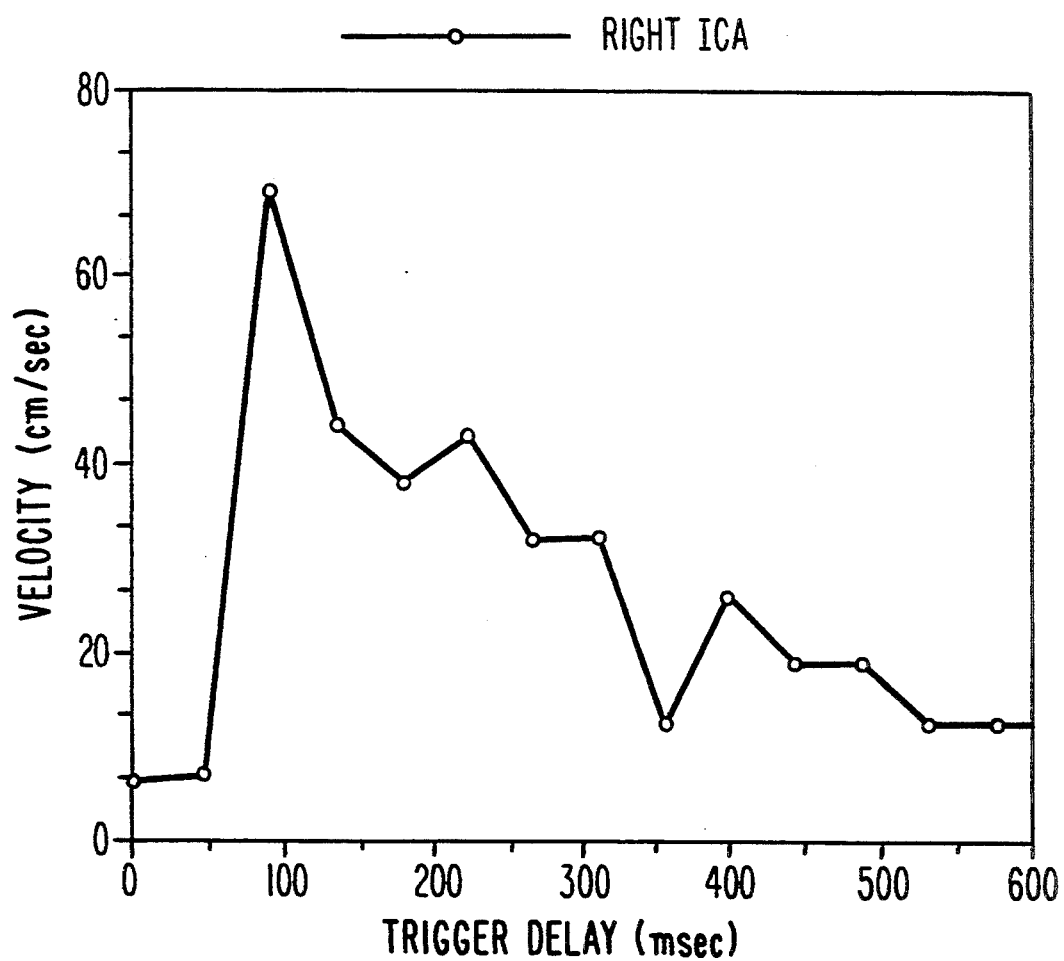
FIG. 19 illustrates flow velocity as a function of trigger delay in the right internal carotid artery by measuring the thickness of the first inflow band in a series of images gated to the cardiac cycle.

FIGS. 18(a) and 18(b) illustrate systolic and diastolic images, respectively, from a set of 15 cardiac phases acquired from the neck of a patient. These gated magnitude gradient-echo images of the internal carotid artery of the patient were obtained using the pulse sequence of FIG. 17. The image plane was chosen so that flow in the internal carotid arteries (ICA) could be measured. Due to the fact that the slice thickness was greater than the diameter of the carotid artery, the observed banding pattern represented the integral of the spin distribution across the artery. The inversion pulse was thus characterized by $G_i=0.2$ gauss/cm, $\omega_i = -2554$ Hz and $T2i=20$ msec. The echo delay, $T_{ed}$, was chosen to be 10 msec, while the strength of the inversion pulse was 80 Hz. The position of the labeling plane is indicated by the horizontal saturation band in the images. As illustrated, there is significantly greater superior displacement of the first labeled band in the systolic image (FIG. 18(a)) than in the diastolic image (FIG. 18(b)). Blood flow in the internal jugular veins is also tagged by the inversion pulse, as indicated by the inferior displacement of a saturation band lateral to the ICA.

Values for peak velocity in the left and right ICA were determined by measuring the maximal length of the first inflow band for each image and dividing by the echo delay, $T_{ed}$. This yielded a total of 15 measurements of flow velocity. The peak velocity measurements for the right ICA are plotted versus trigger delay in FIG. 19, which illustrates flow velocity as a function of trigger delay in the right internal carotid artery of a patient obtained by measuring the thickness of the first inflow band in a series of images gated to the cardiac cycle. The measurements for the left ICA are nearly identical. As shown, the peak blood flow is approximately 70 cm/sec. As shown, the velocity in the ICA never becomes 0, and instead approaches a minimal value of approximately 10 cm/sec. A minimum in the velocity occurs approximately 350 msec after the R wave (after systole). These results generally agree with the findings of Firmin et al. in an article entitled "Echo-Planar High-Resolution Flow Velocity Mapping", *Magnetic Resonance in Medicine*, Vol. 12, pp. 316–327 (1989).

The flow measurement technique of the invention thus provides a simple and robust way to measure fluid flow. It differs fundamentally from other techniques in that motion of the spins during application of the RF pulses is necessary for labeling to occur and in that the width of the inversion bands is directly proportional to the time duration of the inversion pulse. This is in direct contrast to prior art methods which use spatially selective tagging pulses where the thickness of the band is inversely proportional to the time duration of the tagging pulse.

Figure 20:
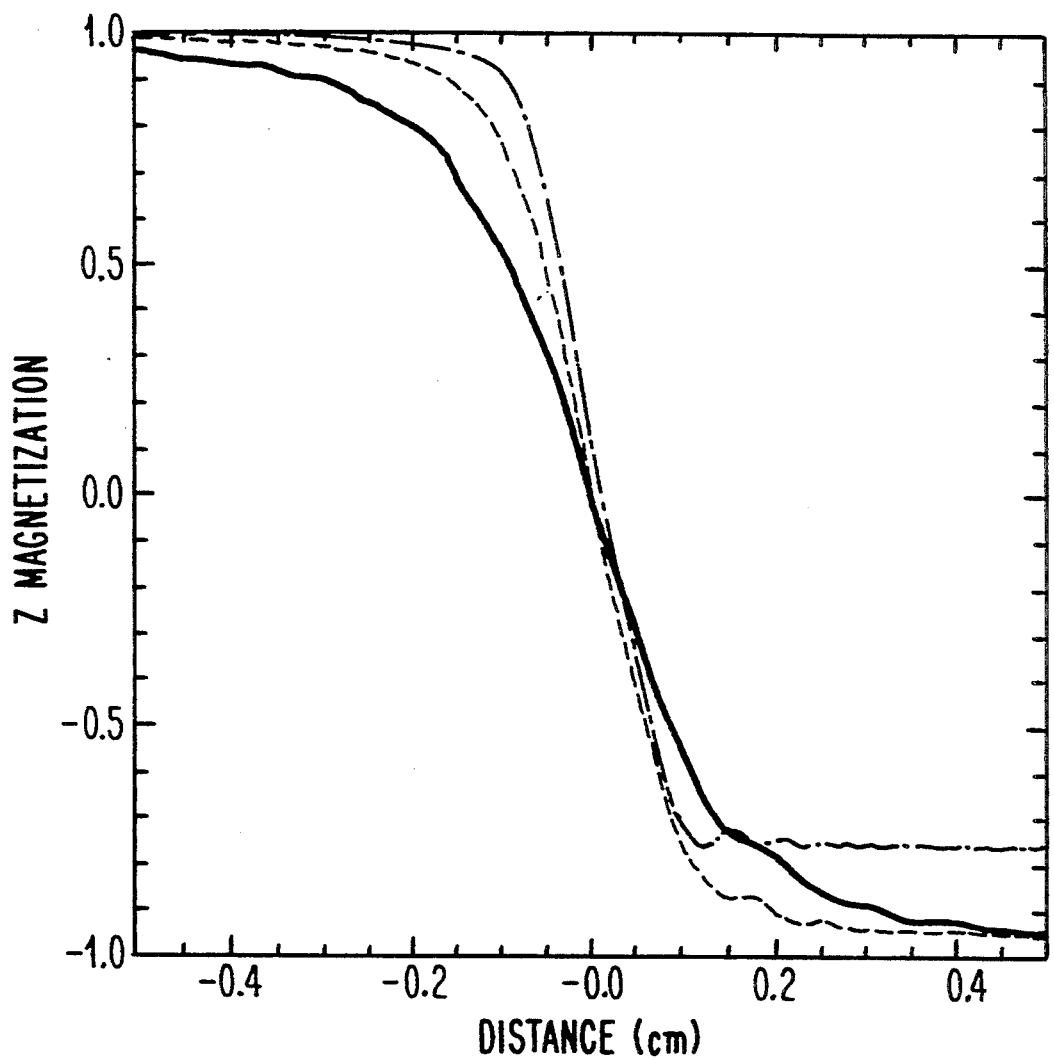
FIG. 20 illustrates pulse simulations of the effect of increasing gradient strength on adiabatic flow inversion in accordance with the invention.

The aforementioned technique of the invention also uses very simple, constant amplitude pulses. Precise band definitions are made possible due to the short frequency interval over which adiabatic inversion typically occurs. FIG. 20 illustrates pulse simulations of the effect of increasing gradient strength on adiabatic flow inversion. In FIG. 20, values of the z-magnetization of a spin moving through a gradient in the presence of a constant RF pulse is plotted as a function of distance from resonance for three different values for the field gradient, $G_i$: 0.1 (solid), 0.2 (dotted) and 0.4 gauss/cm (dashed). For these simulations, the spin velocity was 10 cm/sec and the amplitude of the RF pulse was 60 Hz. As illustrated, at the highest values of the inversion gradient, the distance over which 90% inversion occurs is smallest, less than 1 mm. For lower values of the gradient, the transition becomes less sharp, implying that the banding pattern would be less distinct. FIG. 20 also illustrates, however, that inversion efficiency decreases at the higher gradient strength. Thus, as will be recognized by those skilled in the art, there is generally a trade-off between inversion efficiency and band definition.

An intrinsic limitation of this technique is its inability to measure slow flow. This results from the fact that relaxation effects become significant at the lower sweep rates defined by low velocities. For example, if it is assumed that $T_2=300$ msec, $G_i=0.1$ gauss/cm and $B_i=80$ Hz, then Equation 1 predicts that inversion will fall off for velocities lower than about 1 cm/sec.

RF exposure of the patient may also be minimized in accordance with the technique of the invention by choosing as small a gradient as possible for inversion, while at the same time maintaining reasonable definition between bands. For the gated pulse sequence used in the experiments of Example 3, the average specific absorption rate was approximately 0.05 W/kg, while the peak specific absorption rate was approximately 2.5 W/kg.

The flow measurement technique of the invention thus allows for direct observation of the propagation of many boluses following inversion. The ability to observe the propagation of a larger number of boluses allows one to observe the dynamic effects of turbulence and complex flow. Other benefits of the invention will be apparent to those with ordinary skill in the art.

Although exemplary embodiments of the invention have been described in detail above, those skilled in the art will readily appreciate that many additional modifications are possible in the exemplary embodiments without materially departing from the novel teachings and advantages of the invention. For example, the sequential phase encoding technique of the invention may be used for MR angiography and flow measurement of many other organs, tissues and arteries of the body, including, for example, the kidney, the liver, the lungs, the major arteries and muscles, and the like. In addition, the technique of the invention may be modified by using flow compensated gradient waveforms during acquisition of the observed signal, thereby preserving the signals from the arteries. Those skilled in the art will also appreciate that the MR angiography and blood flow measurement techniques herein described may be combined with the tissue perfusion techniques described in the aforementioned patent application to Williams et al. to provide MR packages which may be used in comprehensive heart, brain or other organ examinations. Accordingly, all such modifications are intended to be included within the scope of this invention as defined in the following claims.

We claim:

1. A method of quantitatively measuring flow in a vessel using magnetic resonance, comprising the steps of:
   (a) applying to said vessel an external substantially uniform magnetic field so as to align predetermined nuclei of a fluid in said vessel with a constant magnetic field gradient of said magnetic field, said predetermined nuclei having a particular resonance frequency;
   (b) applying a substantially constant amplitude tagging radio-frequency (RF) pulse having a frequency different from said particular resonance frequency at an inversion plane in said vessel which is transverse to said magnetic field gradient and transverse to a flow direction of said fluid, said tagging RF pulse being applied in the presence of said constant magnetic field gradient so as to invert spins of those predetermined nuclei which have a component of velocity in a direction of said magnetic field gradient as said predetermined nuclei pass through said inversion plane;
   (c) applying an observation RF pulse for acquiring an image of a band which results as said inverted spins of said predetermined nuclei flow downstream from said inversion plane in said vessel;
   (d) repeating steps (a)–(c) during a predetermined time interval so as to generate a pattern of bands representing inverted spins of nuclei which have flowed downstream from said inversion plane in said vessel during said predetermined time interval; and
   (e) calculating the flow velocity, v, of said fluid in said vessel from the duration, $T_i$, of a particular tagging RF pulse and the length, $\Delta$, of the corresponding band in accordance with the relationship $\Delta = (v)(T_i)$.

2. A method as in claim 1, comprising the further steps of:
   (f) repeating step (e) for each band in said pattern of bands generated during said predetermined time interval; and
   (g) calculating the average velocity of said fluid over a cardiac cycle of a patient using the results of step (f).

3. A method as in claim 1, comprising the further step of applying a homospoil gradient pulse between said tagging and observation RF pulses for attenuating transverse magnetization which develops as a result of said tagging RF pulse.

4. A method as in claim 1, wherein said step (c) includes the step of applying flow compensating gradient waveforms during acquisition of said image.

5. A method as in claim 1, wherein said predetermined time interval is a cardiac cycle of a patient and said method comprises the further step of gating a sequence of said tagging RF pulses and observation RF pulses to the cardiac cycle of the patient.

* * * * *